(12) United States Patent
Bene et al.

(10) Patent No.: US 9,779,212 B2
(45) Date of Patent: Oct. 3, 2017

(54) APPARATUS, PROCESS AND SYSTEM FOR MONITORING A PLURALITY OF PATIENTS AFFECTED BY KIDNEY FAILURE

(71) Applicant: GAMBRO LUNDIA AB, Lund (SE)

(72) Inventors: Bernard Bene, Irigny (FR); Achille Fouilleul, Ruy (FR); Lionel Buttin, Caluire et Cuire (FR)

(73) Assignee: Gambro Lundia AB, Lund (SE)

( * ) Notice: Subject to any disclaimer, the term of this patent is extended or adjusted under 35 U.S.C. 154(b) by 1203 days.

(21) Appl. No.: 13/681,640

(22) Filed: Nov. 20, 2012

(65) Prior Publication Data

US 2013/0317850 A1 Nov. 28, 2013

Related U.S. Application Data

(60) Provisional application No. 61/562,909, filed on Nov. 22, 2011.

(30) Foreign Application Priority Data

Jan. 27, 2012 (IT) .............................. MI2012A0100

(51) Int. Cl.
  *A61M 1/14* (2006.01)
  *G06F 19/00* (2011.01)

(52) U.S. Cl.
  CPC ...... *G06F 19/3406* (2013.01); *G06F 19/3481* (2013.01); *A61M 1/14* (2013.01); *G06F 19/327* (2013.01); *G06F 19/3443* (2013.01)

(58) Field of Classification Search
  CPC . A61M 1/14; A61M 2205/52; A61M 2205/50
  USPC .......... 705/2–3; 707/673; 702/19; 604/4.01, 604/5.01, 6.09, 6.11, 7
  See application file for complete search history.

(56) References Cited

U.S. PATENT DOCUMENTS

| | | | | |
|---|---|---|---|---|
| 6,471,872 | B2 * | 10/2002 | Kitaevich ............... | A61M 1/16 210/134 |
| 6,780,322 | B1 * | 8/2004 | Bissler .................... | A61M 1/16 210/103 |
| 7,072,769 | B2 * | 7/2006 | Fletcher-Haynes . | A61M 1/3496 702/21 |

(Continued)

FOREIGN PATENT DOCUMENTS

| EP | 1 364 666 | 11/2003 |
|---|---|---|
| WO | 2008/087470 | 7/2008 |

*Primary Examiner* — Joy Chng
(74) *Attorney, Agent, or Firm* — Mueting, Raasch & Gebhardt, P.A.

(57) ABSTRACT

An apparatus, a process and a system for monitoring a plurality of patients (P) affected by kidney failure over a time frame (T) are disclosed. The system includes blood treatment units, laboratory storage units, at least one hub module, and client units. The system collects values (VM) of a plurality of session parameters, set values (VS) of a plurality of prescription parameters, values (VL) of a plurality of laboratory parameters and the hub module stores values (KPVi) of selected parameters (KPi) which are a subclass of the collected values (VM, VS, VL) and which are transferred to the client units. Each client unit may define, for each of said patients, a number of indicators (IDk) based on the values (KPVi,k) taken by a respective subclass (KPi,k) of said selected parameters (KPi) and to operate the respective display according to various display modes.

30 Claims, 15 Drawing Sheets

(56) References Cited

U.S. PATENT DOCUMENTS

| | | |
|---|---|---|
| 7,788,038 B2 | 8/2010 | Oshita |
| 2005/0102165 A1* | 5/2005 | Oshita ................ A61M 1/14 705/3 |
| 2010/0145250 A1 | 6/2010 | Bene |
| 2010/0192686 A1* | 8/2010 | Kamen ................ A61M 1/16 73/290 R |
| 2011/0046974 A1* | 2/2011 | Burks ................ G06F 19/3487 705/2 |

* cited by examiner

FIG.11

| Time | QB | Dy | CP | CO | PA | PV | SysP | DiaP | HR | VB | Hb | BV |
|---|---|---|---|---|---|---|---|---|---|---|---|---|
| 07:43:17 | 280 | | | 14.1 | -80 | 35 | | | | | | -1.8 |
| 08:03:43 | 340 | 210 | 14.47 | 14.1 | -130 | 125 | 104 | 59 | 61 | 6.9 | | -2.3 |
| 08:09:07 | 350 | 210 | 14.47 | 14.1 | -140 | 130 | | | | 8.7 | | -4.3 |
| 08:37:24 | 350 | 224 | 14.35 | 14.1 | -135 | 140 | | | | 18.6 | | -3.9 |
| 08:52:13 | 350 | 224 | 14.35 | 14.1 | -140 | 135 | 84 | 55 | 61 | 23.8 | | -4.2 |
| 09:08:43 | 350 | 200 | 14.16 | 14.1 | -140 | 140 | | | | 29.6 | | -5.4 |
| 09:40:02 | 350 | 224 | 14.16 | 14.1 | -135 | 135 | | | | 40.5 | | -5.7 |
| 09:50:07 | 350 | 224 | 14.16 | 14.1 | -140 | 140 | 102 | 58 | 69 | 44.1 | | -6.5 |
| 10:11:23 | 350 | 193 | 14.13 | 14.1 | -140 | 140 | | | | 51.5 | | -7.1 |
| 10:42:52 | 350 | 219 | 14.10 | 14.1 | -145 | 140 | | | | 62.5 | | -7.9 |
| 10:53:08 | 350 | 219 | 14.13 | 14.1 | -145 | 155 | 82 | 57 | 70 | 56.1 | | -7.8 |
| 11:14:11 | 350 | 207 | 14.12 | 14.1 | -140 | 145 | | | | 73.5 | | -7.8 |
| 11:32:23 | 350 | 207 | 14.12 | 14.1 | -140 | 150 | 93 | 36 | 75 | 80.2 | | -7.8 |
| 11:34:32 | 350 | 207 | 14.12 | 14.1 | -140 | 150 | | | | 80.6 | | -8.1 |
| 11:45:33 | 350 | 205 | 14.08 | 14.1 | -145 | 150 | 98 | 65 | 72 | 84.4 | | -8.2 |
| 11:57:53 | 350 | 205 | 14.08 | 14.1 | -145 | 145 | | | | 88.8 | | |

APPARATUS, PROCESS AND SYSTEM FOR MONITORING A PLURALITY OF PATIENTS AFFECTED BY KIDNEY FAILURE

RELATED APPLICATIONS

This application claims the benefit under 35 U.S.C. §119(e) of U.S. Provisional Application No. 61/562,909, filed 22 Nov. 2011 and also claims priority to Italian Application No. MI2012A000100, filed 27 Jan. 2012.

An apparatus, process and system for monitoring a plurality of patients affected by kidney failure are described herein. In one or more embodiments, the apparatus, process and system are configured to monitor a plurality of patients over a time frame such that an operator, e.g. a medical doctor, may be able to more easily survey his patients. In one or more embodiments, the apparatus, process and system may serve, for example, to timely identify those patients who would need a treatment prescription modification, or those patients who would deserve more detailed exams to confirm a potential risk of developing a pathology, etc.

BACKGROUND

It is known that patients affected by kidney failure need to be periodically treated in order to eliminate excess of water and in order to reinstate the proper acid-base and electrolyte equilibrium in blood. These patients may be treated using extracorporeal blood treatment machines which are designed to withdraw blood from a patient, treat the blood and then return the treated blood to the patient.

On occasion of each treatment, a blood treatment machine is properly configured with the disposable components (such as the tubing lines, the hemofilter or dialyzer, the concentrates); then, after few start-up phases, normally including priming of the extracorporeal circuit, a patient's cardiovascular system is connected with the extracorporeal circuit of the blood treatment machine and a number of parameters relating to operation of the machine or to the treatment to be delivered to the patient are set, typically before starting the treatment. Furthermore, in the course of the treatment, a multiplicity of sensors captures the values of a number of sensed parameters which are kept under surveillance. In conclusion, considering that each patient receives 3 or 4 dialysis sessions per week, a relevant number of information is captured and stored on a weekly basis. It should also be noted that patients are often submitted to blood sampling and testing at laboratory units in order to measure concentration of certain substances in blood, which may serve to understand the health status of the patient. In this situation, a huge amount of data is continuously collected for each patient.

It is known to centralize and to make available in specialized clinical information systems the medical status and the dialysis prescription of the patients. In other words, all collected information is kept in databases and a medical doctor willing to have the full picture of a patient may need to consult a huge number of parameter values coming at different moments and from different sources with no possibility to correlate the various parameters to a meaningful clinical picture. This large amount of information may render basically impossible to a medical doctor efficiently identifying relevant information and to correlate certain information with risks to have or contract certain pathologies. Even more difficult is correlating relevant data of one patient with those of other patients: the status of a patient population of a dialysis center is not made available to the medical doctor in a fast and consistent way. To the contrary, data which may refer to a same aspect of the dialysis treatment or of the patient are often scattered in several files, papers and databases. Thus the medical doctor cannot have an overview of the quality of care delivered to his patients and cannot take prompt action at an early stage.

SUMMARY

In one or more embodiments, the apparatus, process and system described herein may offer a technical solution adapted to more easily gather and correlate a variety of information relating to a patient population.

In one or more embodiments, the apparatus, process and system described herein may provide a solution allowing the user to have an efficient tool to visualize a plurality of key aspects related to the status of a relevant number of patients.

In one or more embodiments, the apparatus, process and system described herein may offer a technical solution capable of consolidating in few indicators the overall analysis of patient status thus efficiently storing and/or transferring key information without requiring collection/transmission of huge amount of data.

Furthermore, in one or more embodiments, the apparatus, process and system described herein may render available a technical solution which allows to visualize a number of information with different types of consolidation criteria and which allows easy and intuitive navigation through the various modes of visualization.

Moreover, in one or more embodiments, the apparatus, process and system described herein may be provide a solution adapted to permit reviewing a large population of dialysis patients, orienting the doctors to the patients with the biggest drifts from normality.

In one or more embodiments, the apparatus, process and system described herein may allow an in depth analysis of an impaired quality indicator to provide real time evaluation of the quality of the treatment delivered to the patients.

In one or more embodiments, the apparatus, process and system described herein may provide at least one of the above solutions.

Aspects of one or more embodiments of the apparatus, process and system described herein may are described below.

A 1st aspect concerns, in one or more embodiments, an apparatus of monitoring a plurality of patients (P) affected by kidney failure over a time frame (T), the apparatus comprising a memory (101), a graphic user interface (102), and a control unit (103) connected to the memory and to the graphic user interface, the apparatus being configured for being inserted in a system configured for:
  collecting one or more of:
    values ($V_M$) of a plurality of session parameters measured by sensors of blood treatment machines (300) in the system during respective blood treatment sessions of each patient over said time frame,
    set values ($V_S$) of a plurality of prescription parameters,
    values ($V_L$) of a plurality of laboratory parameters comprising values relating to biological fluid properties obtained from tests conducted on fluid samples taken from each patient over said time frame,
  storing, in a memory (201) of a hub module (200) part of the system, values ($KPV_i$) of selected parameters ($KP_i$) comprising:
    values of a first subgroup of said plurality of session parameters ($V_M$), set values of a second subgroup of said plurality of prescription parameters ($V_S$), and values of a third subgroup of said plurality of laboratory parameters ($V_L$), wherein the apparatus control unit (103) is configured to:

receive and store in the apparatus memory (101), for each patient (P), a prescribed number of the values ($KPV_i$) contained in the hub module memory (201), define, for each of said patients, a number of indicators ($ID_k$) wherein each of said indicator is distinct from the other and is defined based on the values ($KPV_{i,k}$) taken by a respective subclass ($KP_{i,k}$) of said selected parameters ($KP_i$);

operate in a first display mode comprising generating on said graphic user interface (102) a first display (110) having a first selection tool (111) for choosing one among said selected parameters ($KP_i$) and a first display field (112) showing, for each of a plurality of patients, a respective graphic representation (113) of one or more significant values taken by the chosen parameter across said time frame (T);

operate in a second display mode comprising generating on said graphic user interface (102) a second display (120) having a second selection tool (121) for choosing one among said indicators ($ID_k$) and a second display field (122) showing, for one patient, a graphic representation (123) of the values ($KPV_{i,k}$) taken, over the time frame (T), by the subclass of said selected parameters ($KP_{i,k}$) affecting the selected indicator ($ID_k$);

allow, when in said first display mode, choosing one patient and detecting selection of said one patient; and subsequently activate said second display mode and display said second display (120) on the graphic user interface (102) wherein, in the second display mode, graphic representations (123) are displayed of the values ($KPV_{i,k}$) taken, over the time frame (T), by the subclass of said selected parameters ($KP_{i,k}$) affecting the selected indicator ($ID_k$) and relating to the chosen patient.

In a 2nd aspect, according to the 1st aspect, the control unit (103) is, in one or more embodiments, configured to remotely connect with the hub module (200) and receive, at time intervals, the values ($KPV_i$) of selected parameters ($KP_i$) contained in the hub module memory (201).

In a 3rd aspect, according to the 2nd aspect, the control unit (103) is, in one or more embodiments, configured to interrogate the hub module (200) at a plurality of regular time intervals during said time frame (T) in order to collect a plurality of sets of values ($KPV_i$) of selected parameters ($KP_i$), each set referring to a respective time interval.

In a 4th aspect according to any one of the preceding aspects, the control unit (103) is, in one or more embodiments, configured to hide said first display (110) when said second display mode is activated.

In a 5th aspect according to any one of the preceding aspects, the control unit (103) is, in one or more embodiments, configured to display said the representations (113) in side by side relation in said first display field (112).

In a 6th aspect according to any one of the preceding aspects, the control unit (103), in said first display mode, is, in one or more embodiments, configured to detect the patient chosen by detecting selection of one of said first graphic representations (113).

In a 7th aspect according to any one of the preceding aspects, the control unit (103), in said first display mode, is, in one or more embodiments, configured to detect the patient chosen by detecting selection of one of said first graphic representations (113); and detecting selection of one of said graphic representations (113) comprises detecting overlapping of a graphic selector (114) with the chosen one among said first graphic representations, the graphic selector (114) optionally graphically differentiating the chosen first graphic representation from the other first graphic representations displayed on the first display.

In an 8th aspect according to any one of the preceding two aspects, the graphic user interface (102), in one or more embodiments, comprises a touch screen and wherein detecting selection of one of said graphic representations (113) comprises detecting touching of a touch screen area where the graphic representation (113) is displayed.

In a 9th aspect according to any one of the preceding three aspects, detecting selection of one of said graphic representations (113) comprises, in one or more embodiments, detecting entry of a confirmation indicative that the user intends to switch to the second display mode.

In a 10th aspect according to any one of the preceding aspects, the control unit (103) is, in one or more embodiments, configured to display a menu area (130), optionally in the form of a menu bar, comprising a plurality of selectable areas (131, 132, 133), the plurality of selectable areas comprising at least a first selectable area (131) and a second selectable area (132), wherein the control unit is further configured to detect selection of the first selectable area and to activate the first display mode when the first selectable area is selected.

In an 11th aspect according to the preceding aspect, the control unit is, in one or more embodiments, further configured to detect selection of the second selectable area (132) and to activate the second display mode when the second selectable area is selected.

In a 12th aspect according to any one of the preceding two aspects, the control unit (103) is, in one or more embodiments, configured to display the menu area (130) both in said first and in said second display modes.

In a 13th aspect according to the preceding aspect, the control unit (103) is, in one or more embodiments, configured to graphically differentiate the first and second selectable areas respectively when the first or the second display mode is activated to provide a user of a graphic indication of which mode is active.

In a 14th aspect according to any one of the preceding aspects, the first display field (112), in one or more embodiments, comprises a Cartesian representation where one axis (115) represents the patients and one other axis (116) represents the measure of the values taken by the selected parameters ($KP_i$), and wherein each of said first graphic representations (113) comprises a representation of the mean value taken by the selected parameter across said time frame (T) and a graphic representation of a distribution of values taken by the selected parameter around said mean value.

In a 15th aspect according to any one of the preceding aspects, the control unit (103), in said first display mode, is, in one or more embodiments, configured to display on said graphic user interface an auxiliary display (150) comprising a table displaying a list of the monitored patients, the control unit being also configured to associate an identification code to each patient and to detect the patient chosen by detecting selection of the respective identification code.

In a 16th aspect according to any one of the preceding aspects, the control unit (103), in said first display mode, is, in one or more embodiments, configured to display on said graphic user interface a recap display (160) comprising a table (161) displaying a list (162) of monitored patients, a list (163) of said indicators ($ID_k$), and a score (164) associated to a number of indicators and patients, wherein each of the displayed scores is univocally associated to a respective patient and to a respective indicator ($ID_k$), the control unit being configured to calculate each one of said scores (164) based on a comparison of each of the values ($KPV_{i,k}$) taken, for the respective patient, by the subclass of said selected parameters ($KP_{i,k}$) affecting the indicator ($ID_k$), with a respective reference criterion.

In a 17th aspect according to any one of the preceding two aspects, the control unit (103) is, in one or more embodiments, configured to display, when in said first display mode, a switching tool (170) for alternatively displaying one of the first display, the auxiliary display and the recap display.

In a 18th aspect according to the preceding aspect, the control unit (103) is, in one or more embodiments, further configured for associating to each of said scores a different graphic representation, optionally a different background texture, color or a different size, depending upon the score value.

In a 19th aspect according to any one of the preceding aspects, the second selection tool (121) comprises, in one or more embodiments, a plurality of selectable zones (128), each of said selectable zones corresponding to a respective one of said indicators ($ID_k$), wherein the control unit (103) is further configured to:
detect selection of one indicator by detecting selection of the corresponding selectable zone (128), and
display on said second display (120) the graphic representations (123) of the values ($KPV_{i,k}$) taken, over the time frame (T), by the subclass of said selected parameters ($KP_{i,k}$) affecting the selected indicator ($ID_k$) and relating to the chosen patient.

In a 20th aspect according to any one of the preceding aspects, the selectable zones (128), in one or more embodiments, are displayed in side by side relation and define at least one navigation bar.

In a 21st aspect according to any one of the preceding aspects, the control unit (103) is, in one or more embodiments, configured to allow setting of said time frame (T), optionally wherein the control unit is configured to display in said first display mode a time frame selection tool (170) allowing to set at least one of:
a start of said time frame (T),
an end of said time frame (T),
a start and an end of said time frame (T).

In a 22nd aspect according to any one of the preceding aspects, the control unit (103), in one or more embodiments, is configured to allow setting of a population filtration criterion.

In a 23rd aspect according to any one of the preceding aspects, the control unit (103), in one or more embodiments, is configured to:
store in said memory a plurality of population filtration criteria,
display in said first display mode a population filtration tool (180) for the selection of one population filtration criterion;
detect the setting of a population filtration criterion.

In a 24th aspect according to any one of the preceding two aspects, the control unit, when in said first display mode, is configured, in one or more embodiments, to display the respective graphic representation (113) of said one or more significant values, only for those patients satisfying the set population filtration criterion.

In a 25th aspect according to any one of the preceding three aspects, the control unit, when in said first display mode, is, in one or more embodiments, configured to allow choosing one patient only among those satisfying the set population filtration criterion.

In a 26th aspect according to any one of the preceding aspects from 22 to 25 said population filtration criteria, in one or more embodiments, comprises a condition concerning one or more of the values ($KPV_i$) of selected the parameters ($KP_i$).

In a 27th aspect according to any one of the preceding aspects from 22 to 26 said population filtration criteria, in one or more embodiments, comprises conditions concerning one or more of said indicators ($ID_k$).

In a 28th aspect according to any one of the preceding aspects the control unit (103), in one or more embodiments, is configured to:
allow an operator to choose one or more indicators ($ID_k$) of interest,
receive and store in the apparatus memory (101), for each patient (P), only the values ($KPV_i$) contained in the hub module memory (201) taken, over the time frame (T), by the subclass of said selected parameters ($KP_{i,k}$) affecting the chosen indicators ($ID_k$).

In a 29th aspect according to any one of the preceding aspects from 22 to 28, the control unit (103), in one or more embodiments, is configured to request a scan of the hub module memory (201), and receive and store in the apparatus memory exclusively the values ($KPV_i$) of selected parameters ($KP_i$) relating to patients satisfying the population filtration criterion.

In a 30th aspect according to any one of the preceding aspects the control unit, in one or more embodiments, is configured to:
allow, when in said second display mode, a choice of one among the values taken by the parameters of said subclass of selected parameters ($KP_{i,k}$) affecting the selected indicator ($ID_k$);
establish the treatment session corresponding to the chosen value;
operate in a third display mode, comprising generating a third display (140) on said graphic user interface (102) having a third display field (142) showing, for the chosen patient and for the treatment session corresponding to the chosen value, a respective graphic representation (143) of plurality of values taken at different instants over session treatment time by said a plurality parameters.

In a 31st aspect according to any one of the preceding aspects from 16 to 30, the control unit, in one or more embodiments, is configured to calculate a sum and/or a mean value of said scores (164) referring to a same patient.

In a 32nd aspect according to the preceding aspect the control unit, in one or more embodiments, is configured to rank patients from the one having highest score to the one having lowest score.

A 33rd aspect concerns, in one or more embodiments, a process of monitoring a plurality of patients affected by kidney failure over a time frame covering a plurality of blood treatment sessions, the process comprising:
at a hub module (200), receiving for each one of the plurality of patients, values (V) taken by a plurality of patient parameters at different time instants during the time frame (T), said values of the plurality of patient parameters including, for each patient one or more of:
values ($V_M$) of a plurality of session parameters measured by sensors of a blood treatment machine (300) during each blood treatment session of each patient over said time frame, values ($V_L$) of a plurality of laboratory parameters obtained from tests conducted on fluid samples taken from each patient over said time frame (T) and stored in one or more laboratory storage units (400), set values ($V_S$) of a plurality of prescription parameters set for each blood treatment session and each patient on each of said blood treatment machines (300) over said time frame, the hub module (200) being remotely connected to the blood treatment machines (300) and to laboratory storage units (400), the process further comprising:

creating, at hub module, a key parameter log (202) storing the values ($KPV_i$) of selected parameters ($KP_i$) including:
- a first subgroup comprising, for each monitored patient, values of a selection of the plurality of session parameters ($V_M$),
- a second subgroup comprising, for each monitored patient, set values of a selection of the plurality of prescription parameters ($V_S$), and
- a third subgroup comprising, for each monitored patient, values of a selection the plurality of laboratory parameters ($V_L$), defining, either at the hub module or at client units (100) remotely located from the hub module (200), a number of indicators ($ID_k$) for each of said patients, wherein each of said indicators is distinct from the other and is defined based on the values ($KPV_{i,k}$) taken by a respective sub-group ($KP_{i,k}$) of said plurality of patient parameters ($KP_i$);

at client units (100) comparing all or some of the values ($KPV_{i,k}$) taken, over the time frame (T), by the subclasses of selected parameters ($KP_{i,k}$) affecting a same indicator ($ID_k$) with respective reference criteria and signaling whether or not one or more of said criteria are not met.

A 34th aspect concerns, in one or more embodiments, a process of monitoring a plurality of patients affected by kidney failure over a time frame covering a plurality of blood treatment sessions, the process using a hub module (200) remotely connected to the blood treatment machines (300) and to laboratory storage units (400), the hub module comprising a respective control unit (203) and a respective memory, the process comprising:

collecting, for each one of the plurality of patients, values (V) taken by a plurality of patient parameters at different time instants during the time frame (T), said values of the plurality of patient parameters including, for each patient:

values ($V_M$) of a plurality of session parameters measured by sensors of a blood treatment machine (300) during each blood treatment session of each patient over said time frame, values ($V_L$) of a plurality of laboratory parameters obtained from tests conducted on fluid samples taken from each patient over said time frame (T) and stored in one or more laboratory storage units (400), set values ($V_S$) of a plurality of prescription parameters set for each blood treatment session and each patient on each of said blood treatment machines (300) over said time frame, scanning the collected values (V) and selecting values ($KPV_i$) of selected parameters ($KP_i$) comprising:

selecting a first subgroup comprising, for each monitored patient, values of a selection of the plurality of session parameters ($V_M$), selecting a second subgroup comprising, for each monitored patient, set values of a selection of the plurality of prescription parameters ($V_S$), and selecting a third subgroup comprising, for each monitored patient, values of a selection the plurality of laboratory parameters ($V_L$), storing in the hub module memory (201) exclusively the selected values ($KPV_i$) of the selected parameters ($KP_i$);

defining, for each of said patients, a number of indicators ($ID_k$) wherein each of said indicator is distinct from the other and is defined based on the values ($KPV_{i,k}$) taken by a respective sub-group ($KP_{i,k}$) of said plurality of patient parameters ($KP_i$);

at client units (100) remotely located from the hub module (200), receiving the selected values ($KPV_i$) of the selected parameters ($KP_i$) and comparing all or some of the values ($KPV_{i,k}$) taken, over the time frame (T), by the subclasses of selected parameters ($KP_{i,k}$) affecting a same indicator ($ID_k$) with respective reference criteria and signaling whether one or more of said criteria are not met.

A 35th aspect concerns, in one or more embodiments, a system for monitoring a plurality of patients affected by kidney failure over a time frame covering a plurality of blood treatment sessions, the system comprising:

a plurality of blood treatment machines (300) for the treatment of the monitored patients, each blood treatment machine (300) including at least one respective control unit (301) and sensors (302) for measuring session parameters, the control unit of each blood treatment machine being configured to:

receive from the sensors (302) signals corresponding to values ($V_M$) of a plurality of session parameters measured during each blood treatment session for each patient, and receive set values ($V_S$) of a plurality of prescription parameters, said set values of prescription parameters comprising values of a plurality of session parameters which are set on said blood treatment machines for the blood treatment sessions of each patient over said time frame (T);

a number of laboratory storage units (400) configured to store values ($V_L$) of laboratory parameters relating to patient blood properties obtained from tests conducted on fluid samples taken from each patient;

a hub module (200) communicatively connected to the blood treatment machines (300) and to the laboratory storage units (400), the module comprising a control unit (203) configured to:

receive from said blood treatment machines and for each monitored patient, values ($V_M$) of the plurality of session parameters measured by the sensors of each blood treatment machine during each blood treatment session of each patient over said time frame (T), receive from said blood treatment machines and for each monitored patient, set values of ($V_S$) of prescription parameters set for each blood treatment session of each patient over said time frame, receive from the laboratory storage units values ($V_L$) of laboratory parameters obtained from tests conducted on fluid samples taken from each patient over said time frame, and create a key parameter log (202) storing values ($KPV_i$) of selected parameters ($KP_i$) comprising:

values of a first subgroup of said plurality of session parameters ($V_M$), set values of a second subgroup of the plurality of prescription parameters ($V_S$), values of a third subgroup of said plurality of laboratory parameters ($V_L$); and a plurality of client units (100) each configured for reading the data coming from the key parameter log (202) and each further configured to:

store, for each patient, the values ($KPV_i$) of the selected parameters ($KP_i$) contained in the key parameter log (202), define, for each of said patients, a number of indicators ($ID_k$) wherein each of said indicator is distinct from the other and is defined based on the values ($KPV_{i,k}$) taken by a respective subclass ($KP_{i,k}$) of said selected parameters ($KP_i$), compare the values ($KPV_{i,k}$) taken, over the time frame (T), by the subclasses of selected parameters ($KP_{i,k}$) affecting a same indicator ($ID_k$) with respective reference criteria;

signal whether one or more of said criteria are not met.

A 36th aspect concerns, in one or more embodiments, a system for monitoring a plurality of patients affected by kidney failure over a time frame covering a plurality of blood treatment sessions, the system comprising:

a plurality of blood treatment machines (300) for the treatment of the monitored patients, each blood treatment machine (300) including at least one respective control unit (301) and sensors (302) for measuring session parameters, the control unit of each blood treatment machine being configured to:

receive from the sensors (302) signals corresponding to values ($V_M$) of a plurality of session parameters measured during each blood treatment session for each patient, and receive set values ($V_S$) of a plurality of prescription parameters, said set values of prescription parameters comprising values of a plurality of session parameters which are set on said blood treatment machines for the blood treatment sessions of each patient over said time frame (T);

a number of laboratory storage units (400) configured to store values ($V_L$) of laboratory parameters relating to patient blood properties obtained from tests conducted on fluid samples taken from each patient;

a hub module (200) communicatively connected to the blood treatment machines (300) and to the laboratory storage units (400), the module comprising a control unit (203) configured to:

receive from said blood treatment machines and from the laboratory storage units values ($KPV_i$) of selected parameters ($KP_i$) comprising:

values of a first subgroup of said plurality of session parameters ($V_M$), set values of a second subgroup of the plurality of prescription parameters ($V_S$), values of a third subgroup of said plurality of laboratory parameters ($V_L$); and store said values ($KPV_i$) of the selected parameters ($KP_i$) in a hub module memory (201);

a plurality of client units (100) each configured for receiving values ($KPV_i$) of the selected parameters ($KP_i$) coming from the hub module memory (201) and each further configured to:

store, for each patient, the values ($KPV_i$) of the selected parameters ($KP_i$) received from the hub module memory (201), define, for each of said patients, a number of indicators ($ID_k$) wherein each of said indicator is distinct from the other and is defined based on the values ($KPV_{i,k}$) taken by a respective subclass ($KP_{i,k}$) of said selected parameters ($KP_i$), compare the values ($KPV_{i,k}$) taken, over the time frame (T), by the subclasses of selected parameters ($KP_{i,k}$) affecting a same indicator ($ID_k$) with respective reference criteria;

signal whether one or more of said criteria are not met.

In a 37th aspect according to aspect 35 or 36, each client unit is, in one or more embodiments, further configured for interrogating at time intervals (t) the hub module and receiving all or a prefixed number of the values ($KPV_i$) of the selected parameters ($KP_i$) contained in the hub module memory.

In a 38th aspect according to aspect 35 or 36 or 37, the hub module processing unit is, in one or more embodiments, further configured to transmit all or a prefixed number of the values ($KPV_i$) of the selected parameters ($KP_i$) to each of said client units.

In a 39th aspect according to any one of aspects from 35 to 38, the hub module processing unit is, in one or more embodiments, configured to receive from said blood treatment machines and for each monitored patient, set values of ($V_S$) of prescription parameters set for each blood treatment session of each patient over said time frame, said set values of prescription parameters comprising one or more in the group of:

values of a plurality of session parameters set for blood treatment sessions of each patient over said time frame, values representative of medicament prescriptions which have been imparted to each patient over said time frame, values representative of one or more disposable items used during blood treatment sessions of each patient over said time frame.

In a 40th aspect according to any one of aspects from 35 to 39, each client unit, in one or more embodiments, includes an apparatus according to any one of the preceding aspects from 1 to 32.

In a 41st aspect according to any one of aspects from 35 to 40, the system further comprises, in one or more embodiments, an intermediate elaborating unit, the intermediate unit being communicatively interposed between the hub module and the blood treatment machines, wherein the values coming from a number of blood treatment apparatus are collected by the intermediate unit before being transmitted to the hub module, and wherein the intermediate unit is configured to transmit said collected values either at time intervals or upon request to the hub module.

In a 42nd aspect according to any one of aspects from 35 to 41, the system further comprises, in one or more embodiments, a further intermediate elaborating unit, the further intermediate unit being communicatively interposed between the hub module and the number of laboratory storage units, wherein the values coming from a number of laboratory storage units are collected by the further intermediate unit before being transmitted to the hub module, and wherein the further intermediate unit is configured to transmit said collected values either at time intervals or upon request to the hub module.

In a 43rd aspect according to any one of the preceding two aspects, the hub module is, in one or more embodiments, one of:

physically remote from the intermediate unit, physically remote from both the intermediate unit and the further intermediate unit, physically part of the intermediate unit, this latter being remotely connected to the plurality of blood treatment machines, physically part of the further intermediate unit, this latter being remotely connected to the plurality of laboratory storage units.

In a 44th aspect according to aspect 33 or 34, the process, in one or more embodiments, comprises, at each client unit, interrogating at time intervals (t) the hub module and receiving all or a prefixed number of the values ($KPV_i$) of the selected parameters ($KP_i$) contained in the hub module memory.

In a 45th aspect according to aspect 33 or 34 or 44, the hub module, in one or more embodiments, transmits all or a prefixed number of the values ($KPV_i$) of the selected parameters ($KP_i$) to each of said client units.

In a 46th aspect according to aspect 33 or 34 or 44 or 45, the hub module, in one or more embodiments, receives from said blood treatment machines and for each monitored patient, set values of ($V_S$) of prescription parameters set for each blood treatment session of each patient over said time frame, said set values of prescription parameters comprising one or more in the group of:

values of a plurality of session parameters set for blood treatment sessions of each patient over said time frame, values representative of medicament prescriptions which have been imparted to each patient over said time frame, values representative of one or more disposable items used during blood treatment sessions of each patient over said time frame.

In a 47th aspect according to aspect 33 or 34 or 44 or 45 or 46, each client unit, in one or more embodiments, includes an apparatus according to any one of the preceding claims 1-32.

In a 48th aspect according to aspect 33 or 34 or 44 or 45 or 46 or 47, an intermediate elaborating unit is, in one or more embodiments, communicatively interposed between the hub module and the blood treatment machines, wherein the values coming from a number of blood treatment apparatus are collected by the intermediate unit before being transmitted to the hub module, and wherein the intermediate unit transmits said collected values either at time intervals or upon request by the hub module.

In a 49th aspect according to aspect 33 or 34 or 44 or 45 or 46 or 47 or 48, a further intermediate elaborating unit is, in one or more embodiments, communicatively interposed between the hub module and the laboratory storage units, wherein the values coming from a number of laboratory storage units are collected by the further intermediate unit before being transmitted to the hub module, and wherein the further intermediate unit transmits said collected values either at time intervals or upon request to the hub module.

A 50th aspect concerns a system according to aspect 48 or 49, wherein the hub module is, in one or more embodiments, one of:

physically remote from the intermediate unit, physically remote from both the intermediate unit and the further intermediate unit, physically part of the intermediate unit, this latter being remotely connected to the plurality of blood treatment machines, physically part of the further intermediate unit, this latter being remotely connected to the plurality of laboratory storage units.

In a 51st aspect according to any one of the preceding aspects, the values, in one or more embodiments, of the first subgroup of said plurality of session parameters ($V_M$) include measured values for one or more of the following parameters:

blood flow rate,
clearance or dialysance values,
treated blood volume,
K*Tr and or K*Tr/V where K is measured dialysance, Tr is treatment time and V a reference volume,
dialysate conductivity,
patient blood conductivity at the beginning and/or at the end of the treatment session,
transferred ionic mass,
total weight loss,
real session duration,
measures of cardiac parameters: systolic and diastolic arterial pressure (TA), cardiac rate,
arterial and/or venous pressure,
hemoglobin, e.g. obtained by calorimetric detection.

In a 52nd aspect according to any one of the preceding aspects, the set values, in one or more embodiments, of the second subgroup of said plurality of prescription parameters ($V_S$) include, for each blood treatment session of each patient over said time frame T, the following:

duration of the blood treatment session,
blood conductivity,
blood flow rate,
patient's dry weight,
the calcium concentration for the dialysis liquid,
the potassium concentration for the dialysis liquid,
the blood flow rate in the extracorporeal circuit,
the weight loss rate,
the total weight loss to be achieved at the end of the treatment,
the blood conductivity to be achieved at the end of the treatment,
the dialysis dose.

In a 53rd aspect according to any one of the preceding aspects, the prescription parameters, in one or more embodiments, also include values indicative of the disposables used on each session, including values indicative of one or more selected in the group of: the dialyzer used, the tubing set used, the concentrates used to prepare the dialysis liquid, the vascular access used and size thereof.

In a 54th aspect according to any one of the preceding aspects, the values, in one or more embodiments, of the third subgroup of the laboratory parameters ($V_L$) include values of:

Urea concentration (pre and/or post treatment session)
Creatinine concentration (pre and/or post treatment session)
Uric acid concentration (pre and/or post treatment session)
Sodium concentration (pre and/or post treatment session)
Potassium concentration (pre and/or post treatment session)
Bicarbonate concentration (pre and/or post treatment session)
Phosphate concentration (pre and/or post treatment session)
Calcium concentration (pre and/or post treatment session)
Total proteins concentration (pre and/or post treatment session)
PTH (parathyroid hormone)
Hemoglobin
Ferritin Saturation coefficient
Albumin
CRP (C-reactive protein)
Total cholesterol
LDL cholesterol
Triglycerides
Glycemia
beta-2-microglobuline
Glycated hemoglobin
KT/V Urea
Systolic and diastolic arterial pressure (TA) measured while lying on a bed before and after treatment session
Weight before and after treatment session.

In a 55th aspect according to any one of the preceding aspects, the indicators may, in one or more embodiments, comprise from 4 to 8 of the following dialysis indicators:

a first indicator $ID_1$ relating to the conditions of the vascular access—this indicator uses a first subclass of the $KP_i$ including one or more of: measured values $KPV_M$ for the blood flow rate, for the ionic dialysance and for the arterial and venous pressures;

a second indicator $ID_2$ relating to the prescription conformity—this indicator uses a second subclass of the $KP_i$ including one or more of: prescription values $KPV_S$ for the duration of the treatment, the blood and/or dialysate conductivity, the blood flow rate, and the patient's dry weight, and measured values $KPV_M$ for the treated blood volume, for the dialysate conductivity, for the total weight loss and for the total session duration;

a third indicator $ID_3$ relating to potassium—this indicator uses a third subclass of the $KP_i$ including one or more of: prescription values $KPV_S$ for the dialysate potassium and laboratory parameter values $KPV_L$ for the potassium concentration in blood;

a fourth indicator $ID_4$ relating to anemia—this indicator uses a fourth subclass of the $KP_i$ including one or more of: measured values $KPV_M$ for hemoglobin and laboratory parameter values $KPV_L$ for hemoglobin, ferritin and saturation coefficient;

a fifth indicator $ID_6$ relating to nutrition and metabolism—this indicator uses a fifth subclass of the $KP_i$ including one or more of: laboratory parameter values $KPV_L$ bicarbonate, blood sugar, total proteins, albumin, CRP;

a sixth indicator $ID_6$ relating to phosphorous-calcium equilibrium—this indicator uses a sixth subclass of the $KP_i$ including one or more of: laboratory parameter values $KPV_L$ for phosphate, calcium, PTH;

a seventh indicator $ID_7$ relating to hypertension—this indicator uses a seventh subclass of the $KP_i$ including one or more of: prescription values $KPV_S$ for plasmatic conductivity (initial and/or final) and for dialysate conductivity; laboratory parameter values $KPV_L$ for sodium concentration in blood (before and/or after treatment), cardiac parameters (systolic and diastolic pressure, heart rate), weight before and after treatment; and measured values $V_M$ for dialysate conductivity, blood conductivity before and after treatment session, ionic mass transfer, total weight loss, cardiac parameter measures (systolic and diastolic pressure and heart rate);

an eight indicator $ID_8$ relating to dialysis dose—this indicator uses an eight subclass of the $KP_i$ including one or more of: laboratory parameter values $KPV_L$ for urea and creatinine concentration in blood pre and post session and for beta-2-microbuline and KT/V urea; and measured values $V_M$ for the total treated blood volume and the measured KT and KT/V.

In a 56th aspect according to any one of the preceding aspects, the control unit of each of the client units is, in one or more embodiments, configured to compare each of the values ($KPV_{i,k}$) taken, over the time frame T, by the subclasses of selected parameters ($KP_{i,k}$) affecting a same indicator $ID_k$ with respective reference criteria and to detect possible drifts compared to what is regarded as a reference criterion of normality.

In a 57th aspect according to any one of the preceding aspects, the control unit, in one or more embodiments, applies one or more of the following reference criteria in order to classify if the patient's status for each single $ID_k$ is acceptable, not acceptable or lies in an area uncertainty:

for the first indicator $ID_1$: the ionic dialysance measured values are compared with a reference; the patient's status is considered acceptable if the last 3 measures are > than 165 ml/min, not acceptable if the last 3 measures are < than 155 ml/min, and potentially critical in all other cases;

for the second indicator $ID_2$: the status is considered acceptable if the measured values for the parameters affecting this indicator are identical or fall within a strict acceptable range compared to the respective set values;

for the third indicator $ID_3$: the patient's status is considered acceptable if the last 3 measures for the potassium concentration in blood are < than 5.5 mmol/l, not acceptable if the last 3 measures for the potassium concentration in blood are > than 5.5 mmol/l, and potentially critical in all other cases;

for the fourth indicator $ID_3$: the patient's status is considered acceptable if the last 3 values for hemoglobin fall within 10 and 12 g/l; the patient's status is considered not acceptable if the last 3 values for hemoglobin are either above 13 g/l or below 10 g/l; the patient's status is considered potentially critical in all other cases;

for the fifth indicator $ID_5$: the patient's status is considered acceptable if the following conditions are all met:
albumin concentration >32 g/l,
urea concentration >1.1 g/l,
creatinine concentration >60 mg/l,
phosphorus concentration >34 mg/l,
potassium concentration >4.5 mmol/l;
the patient's status is considered not acceptable if the following conditions are all not met:
albumin concentration <32 g/l,
urea concentration <1.1 g/l,
creatinine concentration <60 mg/l,
phosphorus concentration <34 mg/l,
potassium concentration <4.5 mmol/l;
the patient's status is considered potentially critical in all other cases;

for the sixth indicator $ID_6$: the laboratory values for phosphorous, calcium and PTH are compared with respective references; the patient's status is considered acceptable if the last 3 values for phosphorous lie within 34 and 60 mg/l, and the last 3 values for calcium lie within 88 and 100 mg/l, and PTH last value is comprised within 100 and 300 μg/l; the patient's status is considered not acceptable if the last 3 values for phosphorous are above 60 mg/l; the situation is considered potentially critical in all other cases;

for the seventh indicator $ID_7$: the patient's status is considered not acceptable if the last 3 values for pre-dialysis session arterial pressure TA are above 170 mm Hg; the patient's status is considered acceptable if the last 3 values for pre-dialysis session arterial pressure TA are below 150 mm Hg; the patient's status is considered potentially critical in all other cases;

for the eight indicator $ID_8$: the measured KT values are compared with a reference; the patient status is considered acceptable if the last 3 measures are > than 40 liters, not acceptable if the last 3 measures are < than 36 ml/min, and potentially critical in all other cases. In case of less than 3 measures in the last 15 days, then the assessment is not considered reliable and discarded.

In a 58th aspect according to any one of the preceding aspects, the time frame (T) covers, in one or more embodiments, a plurality of blood treatment sessions.

In a 59th aspect according to any one of the preceding aspects, the set values ($V_S$) of a plurality of prescription parameters include, in one or more embodiments, one or more in the group of:

values of a plurality of session parameters set for blood treatment sessions of each patient over said time frame,
values representative of medicament prescriptions which have been imparted to each patient over said time frame, and
values representative of one or more disposable items used during blood treatment sessions of each patient over said time frame.

DESCRIPTION OF THE DRAWINGS

The following drawings are provided by way of non limiting example:

FIG. 11 is a schematic illustration of one illustrative embodiment of a graphic user interface of a client unit part of the system of FIG. 1 or 1A in a third operating mode;

DESCRIPTION OF ILLUSTRATIVE EMBODIMENTS

System

Figure 1:
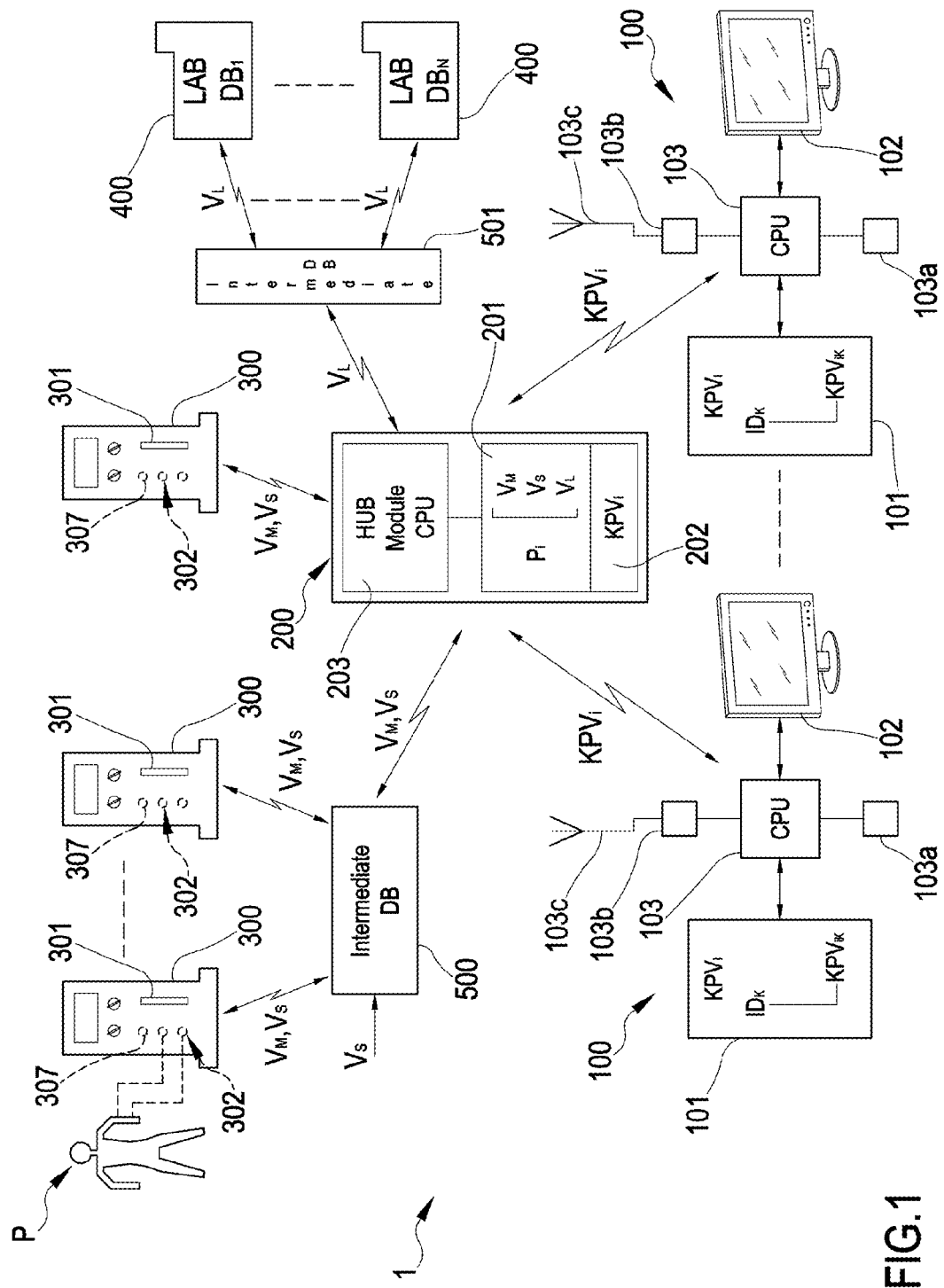
FIG. 1 is a schematic illustration of one illustrative embodiment of a system for monitoring a plurality of patients undergoing extracorporeal blood treatment.
Figure 1A:
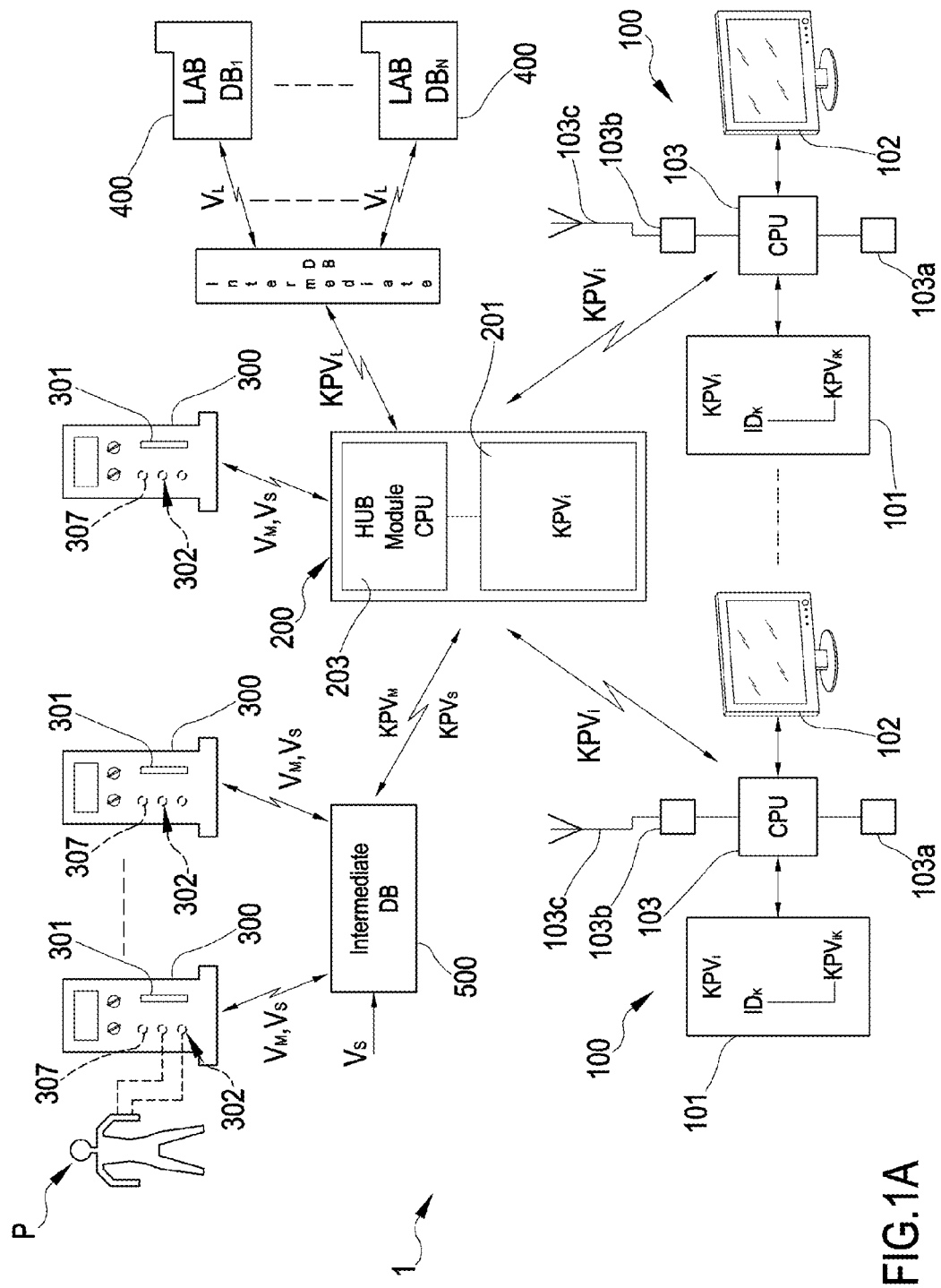
FIG. 1A is a schematic illustration of an alternative embodiment of a system for monitoring a plurality of patients undergoing extracorporeal blood treatment.

With reference to the appended drawing tables, and particularly referring to the illustrative embodiments depicted in FIGS. 1 and 1A, reference numeral 1 and reference numeral 1A respectively indicate a system which is configured for monitoring a plurality of patients affected by kidney failure over a time frame T.

The system 1, 1A comprises a plurality of blood treatment machines 300 for the treatment of the monitored patients. In general, each blood treatment machine includes at least one respective control unit, such as a CPU 301, actuators 307 and sensors 302, such as by way of non limiting example: pressure sensors for instance connected to the blood circuit or to the dialysate circuit, conductivity sensors to measure dialysate conductivity, flow meters for detecting the flow rate through the various machine lines, temperature sensors and so on. The system 1, 1A collects data concerning the plurality of monitored patients P: as it will be explained in detail the collected data concern a plurality of blood treatment sessions executed by said blood treatment machines 300 on the patient(s) as well other data, e.g. coming from sources like laboratories, hospitals etc.

Figure 12:
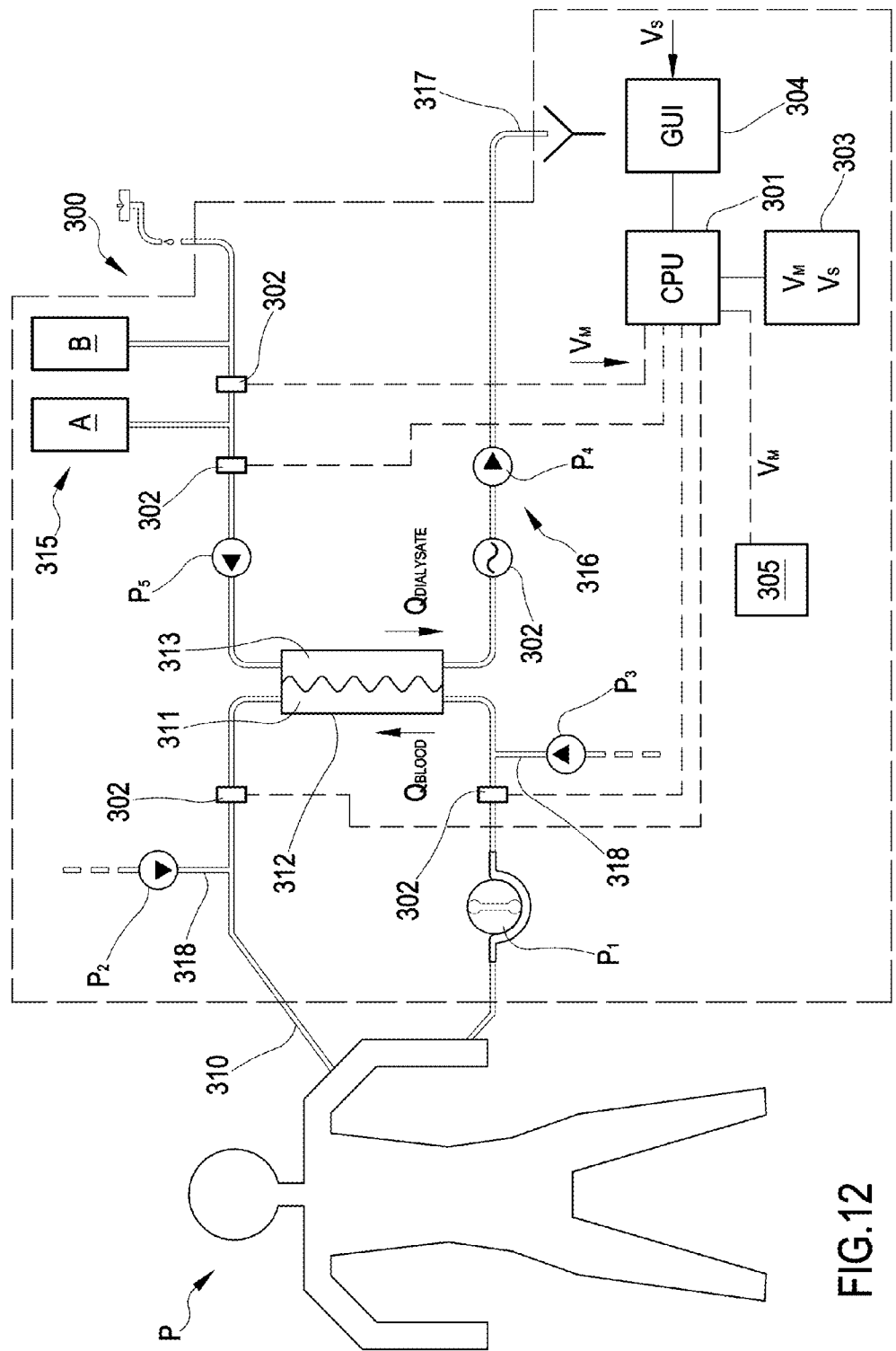
FIG. 12 shows one exemplary embodiment of a blood treatment machine which may be part of the system of FIG. 1 or 1A.

Each blood treatment machine 300 (an exemplary hemodiafiltration machine is shown in FIG. 12—of course machine 300 may be any machine configurable for extracorporeal treatment of blood by ultrafiltration, or hemofiltration, or hemodialysis or hemodiafiltration or other type of blood treatment) may comprise a blood circuit 310 configured for withdrawing blood from a patient P and for returning treated blood to the patient P. The blood circuit includes a blood chamber 311 of a blood treatment unit 312 which also presents a dialysate chamber 313 separated from the blood chamber by a semipermeable membrane 314. The dialysate chamber is connected with a fresh dialysate preparation circuit 315 and with a spent dialysate liquid circuit 316 leading to a waste discharge end 317. One or more infusion lines 318 may be present and be connected to the blood circuit, for instance as shown in FIG. 12. Pumps or other actuators $p_i$ (in the example of FIG. 12, $p_1$ to $p_5$ represent each a respective pump) may act on the blood circuit, on the infusion line(s) on the fresh dialysate circuit 315 (if present), and on the spent liquid circuit 316. The specific design of the blood treatment machine is not material to the present invention and therefore it is not further described in detail: as a matter of fact, any extracorporeal blood treatment machine may be part of the system 1, 1A. In general, sensors 302 measure, either continuously or at time intervals, a significant number of session parameters which are used to monitor the machine and/or to monitor the patient connected to the blood circuit. The control unit of each blood treatment machine is configured to receive from the sensors 302 signals corresponding to measured values, herein collectively indicated as $V_M$, of a plurality of session parameters measured during each blood treatment session for each patient. Typically, the measured values $V_M$ are measured during the course of the treatment and recorded in a memory 303. $V_M$ values may also be acquired via devices 305 distinct but communicatively connected to the machine, such as a pressure detection cuff or an ECG.

In one or more embodiments, the control unit 301 of each blood treatment machine is also configured to receive, for instance via a graphic user interface 304, either at the beginning of the treatment or during the treatment or before treatment starts, set values $V_S$ of a plurality of prescription parameters which the machine shall observe in the course of the treatment. Prescription parameters may include, for example, set values of parameters set on said blood treatment machines which the machine should observe during treatment or achieve by the end of the treatment. The prescription parameters may also include values indicative of the disposables used on each session. Furthermore, the prescription parameters may also include values indicative of possible medicaments prescribed to patients, i.e. medical prescription parameters.

As shown in FIG. 1, 1A the system 1, 1A may also include one or more laboratories (by laboratory it is herein meant any center where blood, or other body fluid, may be analyzed to uncover a predetermined number of properties). Each laboratory comprises or is communicatively connected with a lab storage unit 400 or lab database configured to store values $V_L$ of laboratory parameters relating to patient blood properties obtained from tests conducted on fluid samples taken from each patient. Basically, the laboratory databases include a huge amount of data derived from blood exams conducted on the monitored patients over time: just to mention some these data may include concentrations for a plurality of substances in blood, and various other blood parameters.

At least one a hub module 200 is, in one or more embodiments, connected to the blood treatment machines 300 of the system 1, 1A and to the laboratory storage units 400: the hub module comprises a control unit, such as a control processing unit 203, which is configured to communicate directly or indirectly (e.g. via intermediate units which will herein after described) with the control units of the blood treatment machines and with the processors associated to each laboratory storage unit in order to receive data both from the blood treatment machines and from the laboratory storage units.

More in detail, in the example of FIG. 1 the hub module processing unit, may be configured to receive from said blood treatment machines, and for each monitored patient, the mentioned values $V_M$ of the plurality of session parameters measured by the sensors of each blood treatment machine during each blood treatment session of each patient over said time frame T. Moreover, the hub module processing unit may be configured to receive from said blood treatment machines and for each monitored patient, the set values of $V_S$ of prescription parameters set for each blood treatment session of each patient over said time frame. In particular, the hub module processing unit may be configured to receive from said blood treatment machines and for each monitored patient, set values of $V_S$ of prescription parameters comprising one or more in the group of:
values of a plurality of session parameters set for blood treatment sessions of each patient over said time frame,
values representative of one or more disposable items used during blood treatment sessions of each patient over said time frame,
values representative of medicament prescriptions which have been imparted to each patient over said time frame (note that these last values may be transmitted either by a blood treatment machine or by another unit connected to the system and communicatively linked to the hub module).

Furthermore, the hub module processing unit may, in one or more embodiments, be configured to receive from the laboratory storage units the values $V_L$ of laboratory parameters obtained from tests conducted on fluid samples taken from each patient over said time frame. As it can be understood, particularly if a plurality of patients is being monitored, the amount of data collected by the hub module is huge, considering the number of dialysis sessions per week each patient normally receives and the number of blood exams dialysis patients typically receive on a periodic basis.

In one or more embodiments, the hub module control unit 203 is configured to create a key parameter log 202 where a selection of all data collected by the hub module is stored. In detail, the key parameter log stores values $KPV_i$ of selected parameters $KP_i$ comprising:
values of a first subgroup of said plurality of session parameters $V_M$,
set values of a second subgroup of said plurality of prescription parameters $V_S$, and
values of a third subgroup of said plurality of laboratory parameters $V_L$.

In the alternative embodiment of FIG. 1A, the hub module is, in one or more embodiments, configured to communicate directly or indirectly (e.g., via intermediate units which will herein after described) with the control units of the blood treatment machines and with the processors associated to each laboratory storage unit in order to exclusively receive the values $KPV_i$ of selected parameters $KP_i$ comprising:
values of a first subgroup of said plurality of session parameters $V_M$,
set values of a second subgroup of said plurality of prescription parameters $V_S$, and
values of a third subgroup of said plurality of laboratory parameters $V_L$.

In other words, either the hub module control unit (FIG. 1) receives, in one or more embodiments, all collected values V and makes a selection at the hub module to create the log 202, or the hub module control unit (FIG. 1A) is configured to receive only a selection of the data and store them in the hub memory 201. According to further alternatives, the hub module may, in one or more embodiments, be configured to:
receive all values for $V_M$ values and only the $KPV_i$ values for $V_S$ and $V_L$ values;
receive all values for $V_S$ values and only the $KPV_i$ values for $V_M$ and $V_L$ values;
receive all values for $V_L$ values and only the $KPV_i$ values for $V_S$ and $V_M$ values;
receive all values for $V_M$ and $V_S$ values and only the $KPV_i$ values for $V_L$ values;
receive all values for $V_L$ and $V_S$ values and only the $KPV_i$ values for $V_M$ values;
receive all values for $V_M$ and $V_L$ values and only the $KPV_i$ values for $V_S$ values.

According to one embodiment, the values of the first subgroup of said plurality of session parameters $V_M$, and may include measured values for one or more of the following parameters:
blood flow rate,
clearance or dialysance values,
treated blood volume,
K*Tr and or K*Tr/V where K is measured dialysance, Tr is treatment time and V a reference volume,
dialysate conductivity,
patient blood conductivity at the beginning and/or at the end of the treatment session,
transferred ionic mass,
total weight loss,
real session duration,
measures of cardiac parameters: systolic and diastolic arterial pressure (TA), cardiac rate,
arterial and/or venous pressure,
hemoglobin, e.g. obtained by calorimetric detection.

The set values of the second subgroup of said plurality of prescription parameters $V_S$ may, in one or more embodiments, include for each blood treatment session of each patient over said time frame T one or more of the following:

duration of the blood treatment session,
blood or dialysate conductivity,
blood flow rate,
patient's dry weight,
the calcium concentration for the dialysis liquid,
the potassium concentration for the dialysis liquid,
the blood flow rate in the extracorporeal circuit,
the weight loss rate,
the total weight loss to be achieved at the end of the treatment,
the blood conductivity to be achieved at the end of the treatment,
the dialysis dose.

The prescription parameters may also, in one or more embodiments, indicate the disposables used on each session, including values indicative for instance of: the dialyzer used, the tubing set used, the concentrates used to prepare the dialysis liquid, the vascular access used and size thereof, etc.

Finally, the values of the third subgroup of the laboratory parameters $V_L$ may, in one or more embodiments, include values of:

Urea concentration (pre and/or post treatment session)
Creatinine concentration (pre and/or post treatment session)
Uric acid concentration (pre and/or post treatment session)
Sodium concentration (pre and/or post treatment session)
Potassium concentration (pre and/or post treatment session)
Bicarbonate concentration (pre and/or post treatment session)
Phosphate concentration (pre and/or post treatment session)
Calcium concentration (pre and/or post treatment session)
Total proteins concentration (pre and/or post treatment session)
PTH
Hemoglobin
Ferritin
Saturation coefficient
Albumin
CRP
Total cholesterol
LDL cholesterol
Triglycerides
Glycemia
beta-2-microglobuline
Glycated hemoglobin
KT/V Urea
Systolic and diastolic arterial pressure (TA), before and after treatment session
Heart rate
Weight before and after treatment session.

In other words, the log file 202, or in the case of FIG. 1A the $KPV_i$ values in memory 201, include, in one or more embodiments, an extremely reduced amount of data compared to the collected values $V_S$, $V_M$ and $V_L$.

As shown in FIGS. 1 and 1A, the system 1, 1A also includes, in one or more embodiments, a plurality of client units 100 each configured for reading the data coming from the key parameter log 202 and/or memory 201. The client unit may, in one or more embodiments, be a portable device (such as, e.g., a hand held unit, a laptop, a palmtop, or may be incorporated into a mobile telephone) or may be a fixed unit such as a PC or other unit able to elaborate and display information. The data of the key parameter log of FIG. 1 or in the memory 201 of FIG. 1A may, in one or more embodiments, be copied on a transfer memory which is moved to and read by each client unit: alternatively, the client unit may, in one or more embodiments, be capable of remotely communicating with the hub module, as detailed herein below.

For instance, each or a number of the client units may, in one or more embodiments, be further configured for interrogating at time intervals (t), for instance at regular time intervals, the hub module and receiving updated values $KPV_i$ of the selected parameters $KP_i$ contained in the key parameter log 202 or in memory 201. Alternatively, the hub module may, in one or more embodiments, be configured to dispatch at time intervals a copy of the key parameter values $KPV_i$ to each client unit. In order to establish remote communication any suitable carrier may be used, e.g.: the World Wide Web, a dedicated data line, a radio connection, or combinations thereof. In both cases, the hub module processing unit is configured to either transmit or to prepare for transmission to the client units the values $KPV_i$ of the selected parameters $KP_i$ contained in the key parameter log 202 (FIG. 1) or in the memory 202 (FIG. 1A).

As shown in FIGS. 1 and 1A, the system may, in one or more embodiments, include an intermediate elaborating unit 500 and/or a further intermediate unit 501. If present, the intermediate unit 500 is communicatively interposed between the hub module 200 and some or all the blood treatment machines: in this case, the intermediate unit 500 may work as an intermediate collector for the values $V_S$ and $V_M$ coming from a number of blood treatment apparatus. Note that certain $V_S$ values may also be collected by the intermediate unit 500 via other sources, particularly if the $V_S$ values relating to drug prescriptions to patients. The intermediate unit 500 may then, in one or more embodiments, be configured to transmit either periodically or upon hub module request or upon detection of a command, the collected values to the hub module.

If present, the further intermediate unit 501 is, in one or more embodiments, communicatively interposed between the hub module 200 and some or all the laboratory databases: in this case the further intermediate unit 501 may work as an intermediate collector for the values $V_L$ coming from a number of laboratory databases. The further intermediate unit 501 may then be configured to transmit, in one or more embodiments, either periodically or upon hub module request or upon detection of a command the collected values to the hub module.

The Client Units

Each client unit 100 comprises, in one or more embodiments, at least one respective control unit (such as CPU 103) configured to store, for each patient, the values $KPV_i$ of the selected parameters $KP_i$ contained in the key parameter log 202 (FIG. 1) or in the memory 201 (FIG. 1A). The control unit 103 is, in one or more embodiments, further configured to define, for each of said patients, a number of indicators $ID_k$ wherein each of said indicator is distinct from the other and is defined based on the values $KPV_{i,k}$ taken by a respective subclass $KP_{i,k}$ of said selected parameters $KP_i$.

Each indicator is designed to provide the operator with information, (e.g., clear and immediate information) on the status of a key aspect of the dialysis treatment delivered to a specific patient. In accordance with one or more embodiments, up to eight (8) dialysis indicators $ID_k$ may be defined by each control unit or CPU 103, as follows:

a first indicator $ID_1$ relating to the conditions of the vascular access—this indicator may, in one or more embodiments, use a first subclass of the $KP_i$ including:

measured values $KPV_M$ for the blood flow rate, for the ionic dialysance and for the arterial and venous pressures;

a second indicator $ID_2$ relating to the prescription conformity—this indicator may, in one or more embodiments, use a second subclass of the $KP_i$ including: prescription values $KPV_S$ for the duration of the treatment, the blood and/or dialysate conductivity, the blood flow rate, and the patient's dry weight, and measured values $KPV_M$ for the treated blood volume, for the dialysate conductivity, for the total weight loss and for the total session duration;

a third indicator $ID_3$ relating to potassium—this indicator may, in one or more embodiments, use a third subclass of the $KP_i$ including: prescription values $KPV_S$ for the dialysate potassium and laboratory parameter values $KPV_L$ for the potassium concentration in blood;

a fourth indicator $ID_4$ relating to anemia—this indicator may, in one or more embodiments, use a fourth subclass of the $KP_i$ including: measured values $KPV_M$ for hemoglobin and laboratory parameter values $KPV_L$ for hemoglobin, ferritin and saturation coefficient;

a fifth indicator $ID_5$ relating to nutrition and metabolism—this indicator may, in one or more embodiments, use a fifth subclass of the $KP_i$ including: laboratory parameter values $KPV_L$ bicarbonate, blood sugar, total proteins, albumin, CRP;

a sixth indicator $ID_6$ relating to phosphorous-calcium equilibrium—this indicator may, in one or more embodiments, use a sixth subclass of the $KP_i$ including: laboratory parameter values $KPV_L$ for phosphate, calcium, PTH;

a seventh indicator $ID_7$ relating to hypertension—this indicator may, in one or more embodiments, use a seventh subclass of the $KP_i$ including: prescription values $KPV_S$ for plasmatic conductivity (initial and/or final) and for dialysate conductivity; laboratory parameter values $KPV_L$ for sodium concentration in blood (before and/or after treatment), cardiac parameters (systolic and diastolic pressure, heart rate), weight before and after treatment; and measured values $V_M$ for dialysate conductivity, blood conductivity before and after treatment session, ionic mass transfer, total weight loss, cardiac parameter measures (systolic and diastolic pressure and heart rate);

an eighth indicator $ID_8$ relating to dialysis dose—this indicator may, in one or more embodiments, use an eighth subclass of the $KP_i$ including: laboratory parameter values $KPV_L$ for urea and creatinine concentration in blood pre and post session and for beta-2-microglobuline and KT/V urea; and measured values $V_M$ for the total treated blood volume and the measured KT and KT/V.

In one or more embodiments, each of the values $KPV_{i,k}$ taken, over the time frame T, by the subclasses of selected parameters $KP_{i,k}$ affecting a same indicator $ID_k$ may be compared with respective reference criteria in order to detect possible drifts compared to what is regarded as normality.

For instance, referring to the above eight indicators $ID_k$ the control unit may, in one or more embodiments, be configured to apply the following reference criteria in order to classify if the patient's status for each single $ID_k$ is acceptable, not acceptable or lies in an area uncertainty (potentially critical):

for the first indicator $ID_1$: the ionic dialysance measured values are compared with a reference; the patient's status is considered acceptable, in one or more embodiments, if, e.g., the last 3 measures are greater than 165 ml/min, not acceptable if, e.g., the last 3 measures are less than 155 ml/min, and potentially critical in all other cases. In case of, e.g., less than 3 measures in the last 15 days, then the assessment is, in one or more embodiments, not considered reliable and discarded;

for the second indicator $ID_2$: the status is considered acceptable if, in one or more embodiments, all the measured values (e.g. treated blood volume, dialysate conductivity, total weight loss and total treatment time) are identical or fall within a strict acceptable range compared to the respective set values;

for the third indicator $ID_3$: the patient's status is, in one or more embodiments, considered acceptable if the last 3 measures for the potassium concentration in blood are, e.g., less than 5.5 mmol/l, not acceptable if, e.g., the last 3 measures for the potassium concentration in blood are greater than 5.5 mmol/l, and potentially critical in all other cases;

for the fourth indicator $ID_4$: the patient's status is, in one or more embodiments, considered acceptable if the last 3 values for hemoglobin fall within, e.g., 10 and 12 g/l; the patient's status is considered not acceptable if the last 3 values for hemoglobin are either above, e.g., 13 g/l or below, e.g., 10 g/l; the patient's status is considered potentially critical in all other cases;

for the fifth indicator $ID_5$: the patient's status is, in one or more embodiments, considered acceptable if the following conditions are all met:
albumin concentration >32 g/l,
urea concentration >1.1 WI,
creatinine concentration >60 mg/l,
phosphorus concentration >34 mg/l,
potassium concentration >4.5 mmol/l;
the patient's status is considered not acceptable if the following conditions are all not met:
albumin concentration <32 g/l,
urea concentration <1.1 WI,
creatinine concentration <60 mg/l,
phosphorus concentration <34 mg/l,
potassium concentration <4.5 mmol/l;
the patient's status is considered potentially critical in all other cases;

for the sixth indicator $ID_6$: the laboratory values for phosphorous, calcium and PTH are compared with respective references; the patient's status is, in one or more embodiments, considered acceptable if the last 3 values for phosphorous lie within, e.g., 34 and 60 mg/l, and the last 3 values for calcium lie within, e.g., 88 and 100 mg/l, and PTH last value is comprised within, e.g., 100 and 300 µg/l; the patient's status is considered not acceptable if the last 3 values for phosphorous are above, e.g., 60 mg/l; the situation is considered potentially critical in all other cases;

for the seventh indicator $ID_7$: the patient's status is, in one or more embodiments, considered not acceptable if the last 3 values for pre-dialysis session arterial pressure TA are above, e.g., 170 mm Hg; the patient's status is considered acceptable if the last 3 values for pre-dialysis session arterial pressure TA are below, e.g., 150 mm Hg; the patient's status is considered potentially critical in all other cases;

for the eight indicator $ID_8$: the measured KT values are compared with a reference; the patient status is, in one or more embodiments, considered acceptable if the last 3 measures are, e.g., greater than 40 liters, not acceptable if the last 3 measures are, e.g., less than 36 ml/min, and potentially critical in all other cases. In case of less than 3 measures in the last 15 days, then the assessment is, in one or more embodiments, not considered reliable and discarded.

Although above criteria may have slight variations depending upon the implementation, it should be noted that there exist, in one or more embodiments, a plurality of dialysis indicators having acceptance criteria using—at the same time values of a plurality of parameters—to establish whether a patient's status is acceptable or not.

The control unit or CPU 103 may, in one or more embodiments, be configured to signal whether one or more of said criteria are met or not; in practice the control unit may be programmed to issue a warning signal for activating an alarm in case of drift of one or more indicators from respective normality criteria (acceptable); the alarm may be acoustic or visual: depending on the type of alarm the control unit shall cooperate with corresponding visual actuators (such as speakers or buzzers) or acoustic actuators (such as dedicated lamps or parts of the display of the GUI conveniently activated by the control unit); the control unit 101 may also, in one or more embodiments, be configured to indicate, via a user interface, whether each criterion is non-acceptable or only potentially susceptible of being problematic, as it will be described herein below. Going back to FIGS. 1 and 1A, each client unit 100 is, in one or more embodiments, an apparatus comprising a memory 101, a graphic user interface 102 and a control unit 103 connected to the memory and to graphic user interface. As already shortly described, each client unit 100 is, in one or more embodiments, configured for receiving and interpreting data (the $KPV_i$) contained in the key parameter log 202 or in the memory 201 of the above described hub module. In further detail, the control unit 103 may, in one or more embodiments, be configured to receive and store in the client unit memory 101, for each patient P, the values $KPV_i$ contained in the key parameter log 202, and define, for each of said patients, the plurality of distinct dialysis indicators $ID_k$ wherein each of said indicator is defined based on the values $KPV_{i,k}$ taken by a respective subclass $KP_{i,k}$ of said selected parameters $KP_i$.

Figure 2:
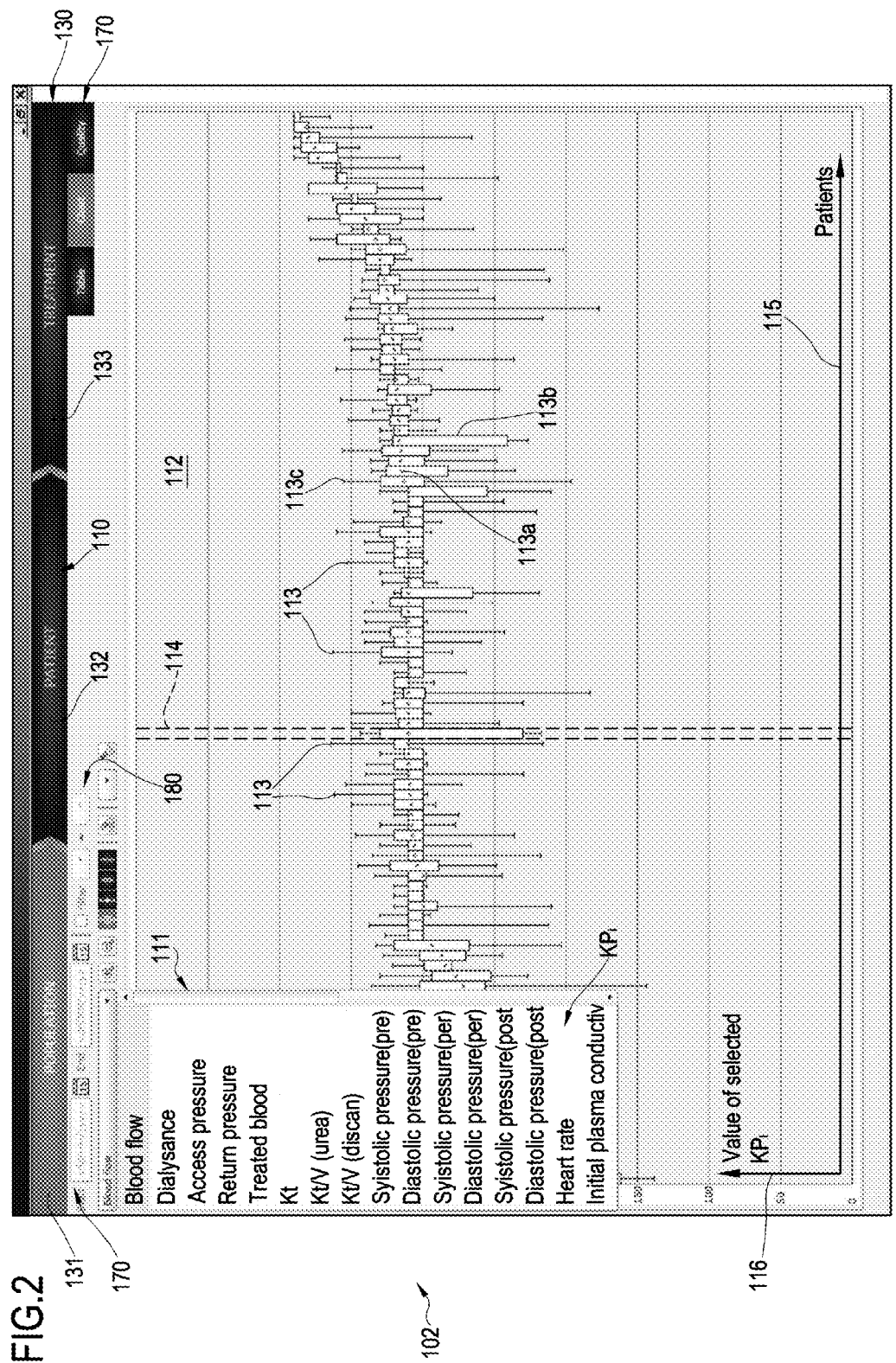
FIG. 2 is a schematic illustration of one illustrative embodiment of a graphic user interface of a client unit part of the system of FIG. 1 in a first operating mode.

With reference to FIGS. from 2 to 10, the control unit government of the graphic user interface 102 so as to provide the user with a tool consolidating only relevant information and in an easy to use and comprehend manner is, in one or more embodiments, described. With reference to FIG. 2, it can be seen that the control unit 103 may, in one or more embodiments, be configured to operate in a first display mode: in this first display mode the control unit generates on the graphic user interface 102 a first display 110 comprising, in one or more embodiments, a first selection tool 111 (for instance in the form of a drop down menu) for choosing one among the selected parameters $KP_i$. The control unit also, in one or more embodiments, displays a first display field 112 showing, for each of a plurality of patients, a respective graphic representation 113 (for instance in the form of a vertical bar) of one or more significant values taken by the chosen parameter across said time frame (T); in the example of FIG. 2 the first selection tool is a drop down menu which elements may be selected using a pointer, such as, e.g., a mouse-controlled or keyboard controlled pointer, or directly touching the selection area if the graphic user interface is presented on a touch screen. The first display field may, in one or more embodiments, be substantially rectangular and may occupy the major part of the visual area of the GUI; moreover, the first display field 112 may comprise a Cartesian representation where one axis 115 represents the patients and one other axis 116 represents the measure of the values taken by the selected parameters $KP_i$. In the example of FIG. 2, each first graphic representation 113 comprises, in one or more embodiments, a representation (e.g. a point 113a) indicative of the mean value taken by the selected parameter across said time frame (T) and a graphic representation (e.g. a bar 113b) indicative of the distribution of values taken by the selected parameter around said mean value. The bar 113b in FIG. 2 represents the distribution of a certain percentage (e.g., 80%) of the values around the mean value, while a segment 113c, vertically longer than the bar, indicates the maximum and minimum values for the $KP_i$ selected with the selection tool 111 (in FIG. 1 blood flow is the selected $KP_i$).

Figure 3:
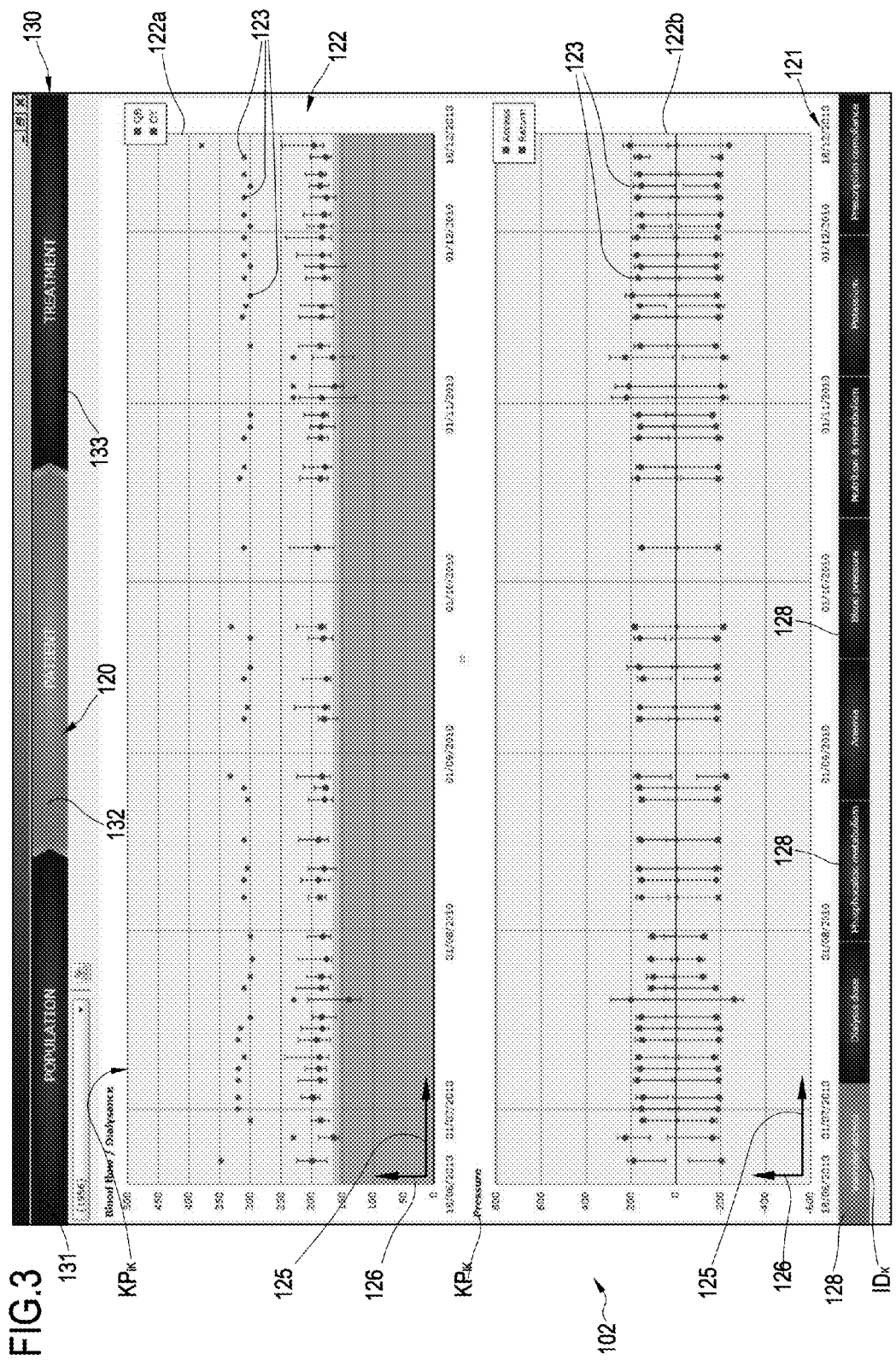
FIGS. 3 and 5 to 10 are schematic illustrations of illustrative embodiments of a graphic user interface of a client unit part of the system of FIG. 1 or 1A in a second operating mode.
Figure 9:
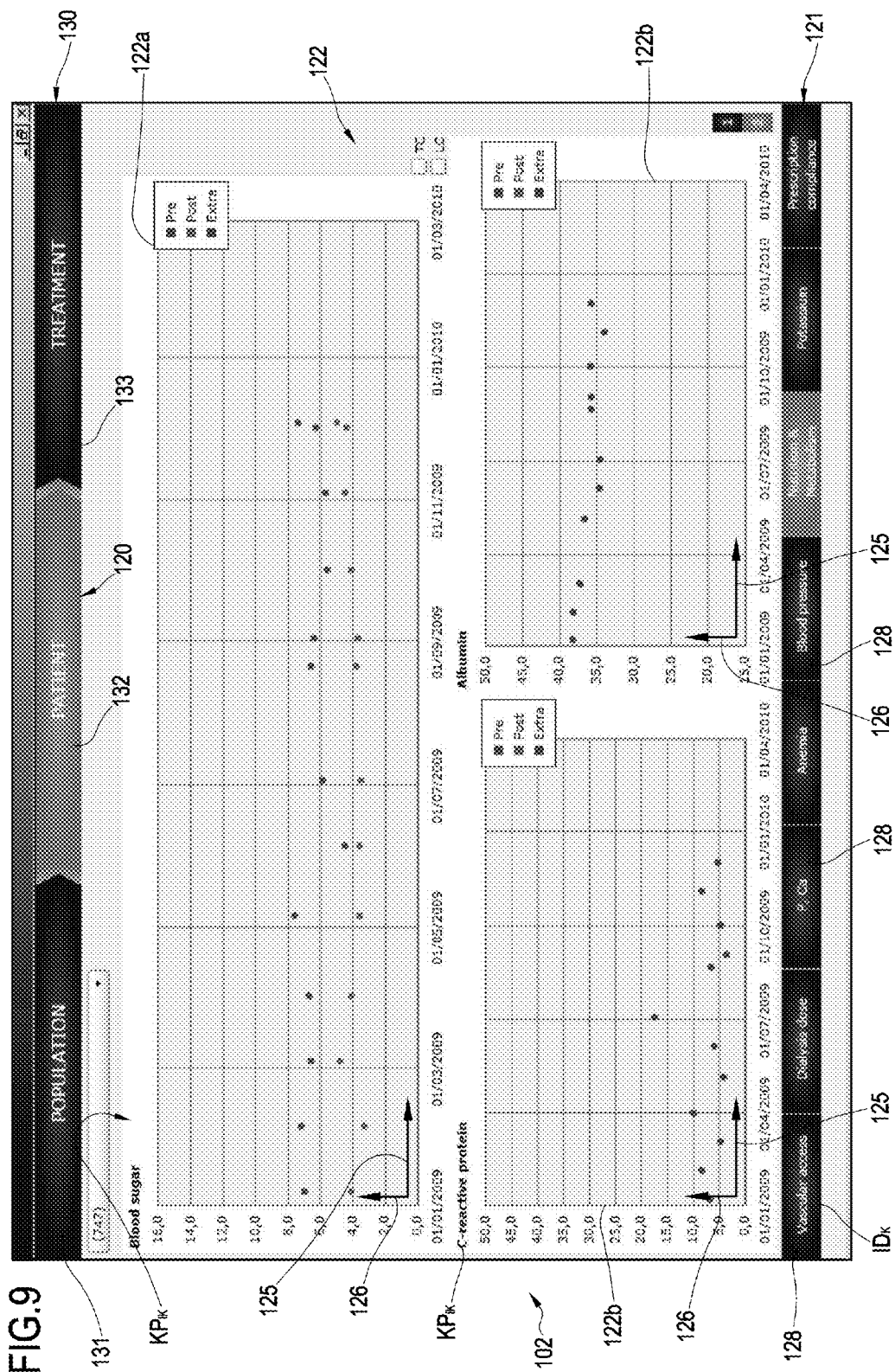
Figure 10:
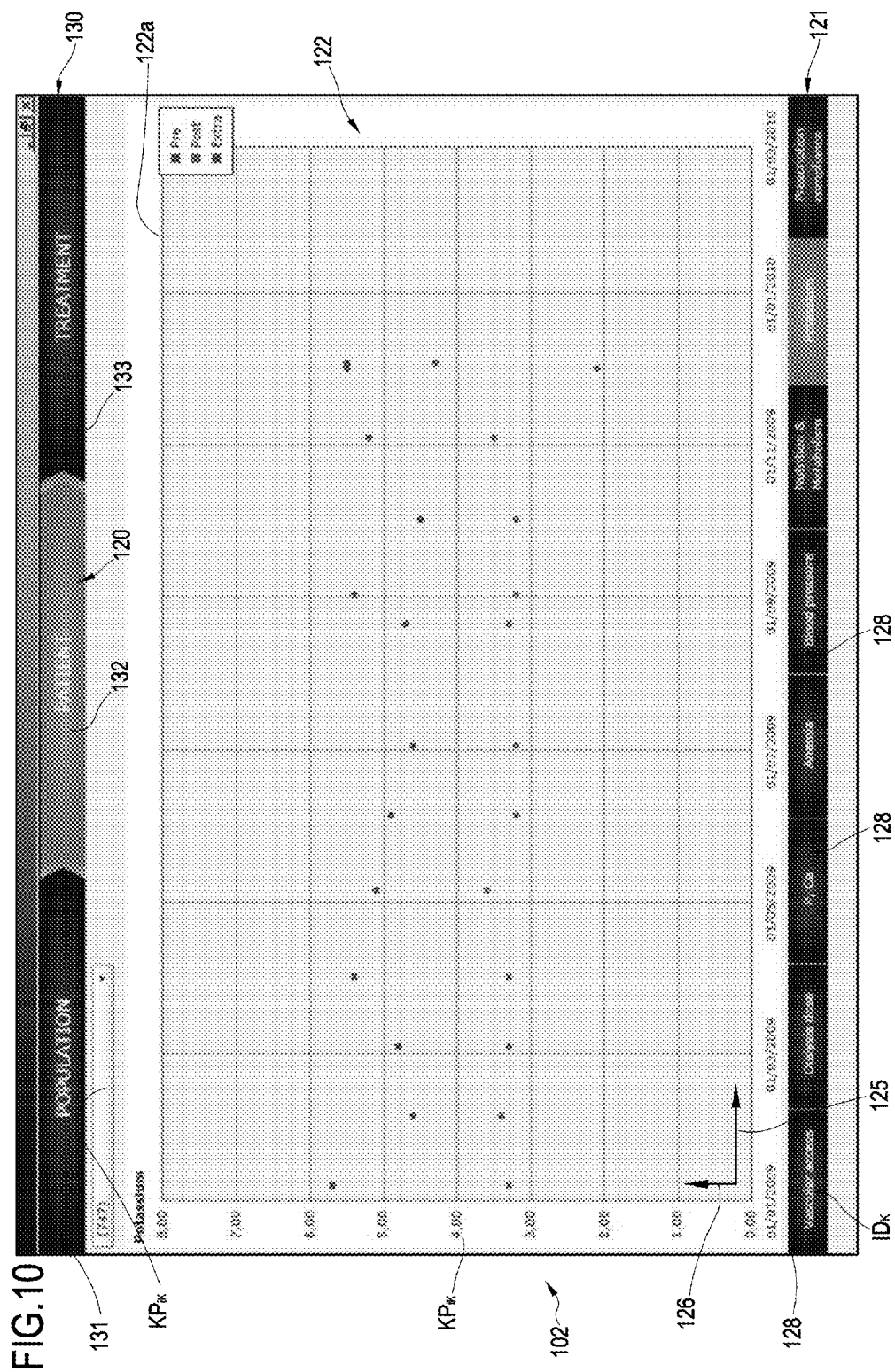

As shown in FIG. 3, the control unit is, in one or more embodiments, also configured for switching to a second display mode: in this second mode the control unit 103 is, in one or more embodiments, configured to generate on said graphic user interface 102 a second display 120 comprising a second selection tool 121 for choosing one among the indicators $ID_k$. The second selection tool 121 may comprise a plurality of selectable zones 128 (in the case shown in the figures, there are eight (8) indicators and, therefore, eight (8) possible selection zones in tool 121): each of said selectable zones corresponds to a respective one of said indicators $ID_k$. For instance, the selectable zones 128 may, in one or more embodiments, be displayed in side by side relation to define a navigation bar. The control unit 103 may, in one or more embodiments, be configured to detect selection of one indicator by detecting selection of the corresponding selectable zone 128, and display on the second display field 122 of second display 120 the graphic representations 123 of the values $KPV_{i,k}$ taken, over the time frame T, by the subclass of said selected parameters $KP_{i,k}$ affecting the selected indicator $ID_k$ and relating to the chosen patient (as selected in the first display mode). For instance, in FIG. 3, the selected indicator in tool 121 is 'vascular access' and the values $KPV_{i,k}$ of $KP_{i,k}$ affecting indicator 'vascular access' are dialysance, blood flow and arterial and venous pressure which are presented in a Cartesian representation where the X-axis 125 represents time and the Y-axis 126 represents the value $KPV_{i,k}$. Depending upon the case, the second display field may include, e.g., two or more separate display areas: display areas 122a and 122b are for instance visible in FIG. 3, while the second display includes display areas 122a, 122b and 122c in FIG. 9; each display area is, e.g., used for displaying values measurable with a same unit: in the case of FIG. 3, pressures are in displayed area 122b while dialysance and blood flow rate are in display area 122a.

FIGS. 5 to 10 are analogous to FIG. 3 and represent the second display fields which the control unit is, in one or more embodiments, configured to display upon selection of the respective item in the selection tool 121.

In one or more embodiments, the control unit in said first display mode may be configured to allow choosing one patient and to detect selection of said one patient. As a consequence of detecting selection of one patient, the control unit is, in one or more embodiments, configured to activate the second display mode thus displaying the second display on the graphic user interface. In the second display mode, the control unit displays, in one or more embodiments, the graphic representations 123 of the values $KPV_{i,k}$ taken, over the time frame T, by the subclass of the selected parameters $KP_{i,k}$ affecting the selected indicator $ID_k$ and relating to the chosen patient. In practice, while in the first display mode the user is in condition to select the patient and to cause switching to the second display mode: then when in the second display mode a detection is made of the selected item in selection tool 121 and thus the corresponding values $KPV_{i,k}$ are displayed; note that in the example shown, the control unit 103 is configured to hide the first display 110 when the second display mode is activated.

Going into further detail, the control unit 103 may, in one or more embodiments, be configured to display the representations 113 in side by side relation in said first display field 112 and to detect the patient chosen by detecting selection of one of said first graphic representations 113. The selection may occur in various alternative ways, e.g., by detecting overlapping of a graphic selector 114 with the chosen one among said first graphic representations; the graphic selector 114 may be any item graphically differentiating the chosen first graphic representation from the other first graphic representations displayed on the first display. Alternatively, when the graphic user interface 102 comprises a touch screen, then detecting selection of one graphic representation 113 may comprise detecting touching of a touch screen area where the graphic representation 113 is displayed. Note that the switch to the second display mode may occur automatically upon patient selection or after detecting entry of a confirmation (such as a pressing a further soft or hard confirmation key part of the user interface) indicative that the user really intends to switch to the second display mode. In addition or as a further alternative, the control unit 103 may, in one or more embodiments, be configured to display a menu area 130, e.g. in the form of a menu bar, comprising a plurality of selectable areas including, e.g., a first selectable area 131 and a second selectable area 132 and an optional third selectable area 133. The control unit may, in one or more embodiments, be programmed to detect selection of the first selectable area and to activate the first display mode when the first selectable area is selected and to detect selection of the second selectable area 132 and to activate the second display mode when the second selectable area is selected. In other words, the bar 130 would, e.g., work as a navigation bar across display modes: when switching to the second mode the selected patient and selected indicator are taken into account for the purpose of displaying the proper data. Note that in the example shown in the appended figures, the control unit 103 is, in one or more embodiments, configured to display the menu area 130 both in said first and in said second display modes and to graphically differentiate the first and second selectable areas respectively when the first or the second display mode is activated to provide a user with a graphic indication of which mode is active.

In one or more embodiments, the control unit 103 (see FIG. 4), when in said first display mode, may be configured to display on said graphic user interface an auxiliary display 160 comprising a table 161 displaying a list 162 of the monitored patients, the control unit being also configured to associate an identification code to each patient and to detect the patient chosen by detecting selection of the respective identification code. Moreover, the auxiliary display 160 may, in one or more embodiments, have a recap format comprising a table 161 (again refer to FIG. 4) displaying a list 162 of monitored patients, a list 163 of said indicators $ID_K$, and a score 164 associated to a number of indicators and patients. Each of the displayed scores is, in one or more embodiments, univocally associated to a respective patient and to a respective indicator $ID_K$ and depends upon the outcome of the above described acceptance criteria for each dialysis indicator: the control unit may also be configured to calculate each one of said scores 164 based on a comparison of each of the values $KPV_{i,k}$ taken, for the respective patient, by the subclass of said selected parameters $KP_{i,k}$ affecting the indicator $ID_k$, with a respective reference criterion as described for the 8 indicators above. In practice a first score (e.g., zero) may, in one or more embodiments, be associated in case the acceptance criteria is met, a second score (e.g.: two) may be associated if a certain criterion is not met, and an intermediate score (e.g.: one) in all other situations. The control unit may, in one or more embodiments, be configured to associate a respective graphic representation to each score: for instance, each code may have a different background texture, color or a different size, depending upon the score value. In the example shown in FIG. 4, a green background color may be associated to a score=0 (meaning an acceptable condition), a yellow background color to a score=1 (meaning an intermediate situation) and a red background color to a score=2 (meaning a non-acceptable condition).

Figure 4:
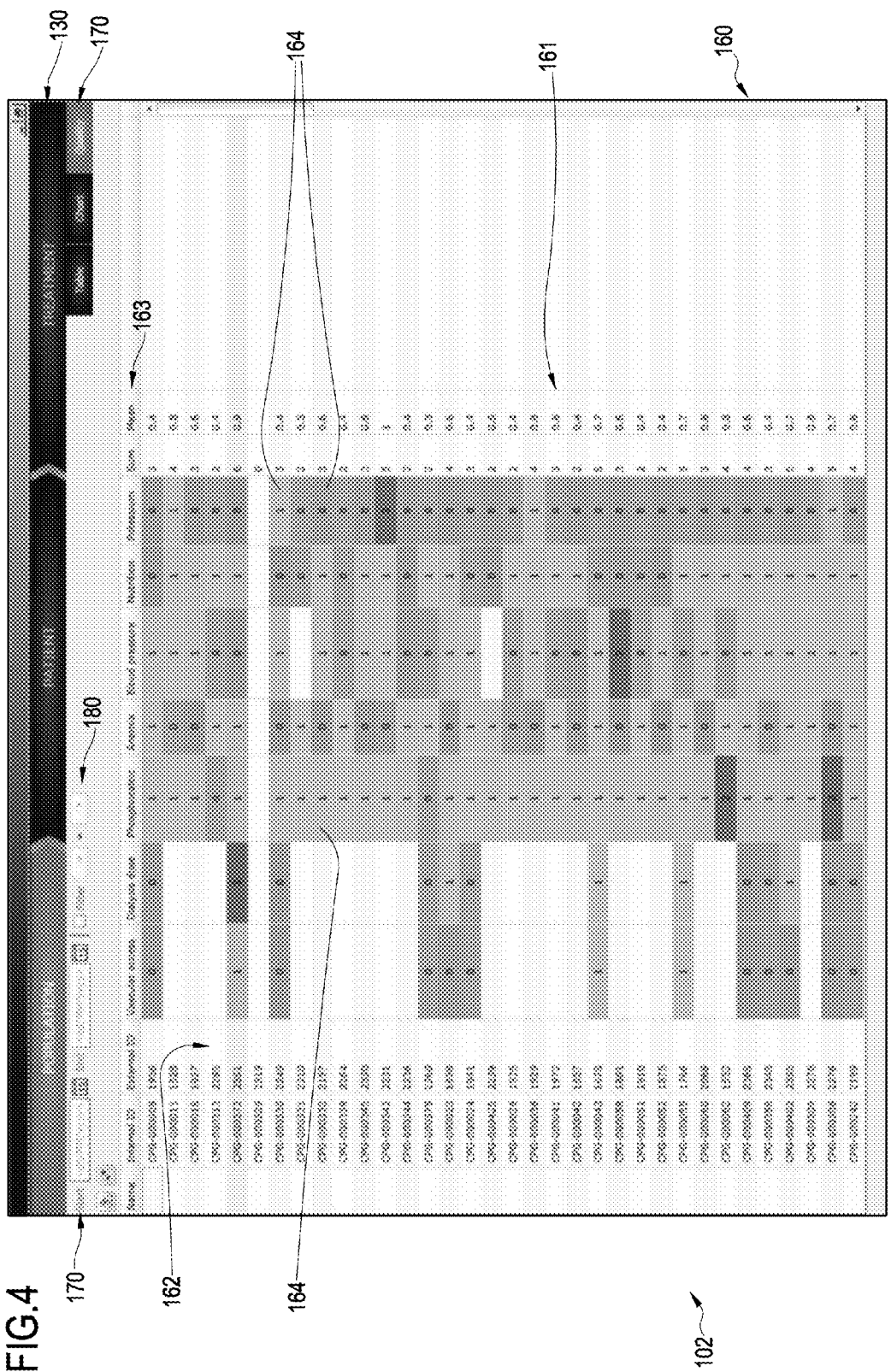
FIG. 4 is a schematic illustration of one illustrative embodiment of a graphic user interface of a client unit part of the system of FIG. 1 or 1A in a first operating mode with a screen different from that of FIG. 2.
Figure 5:
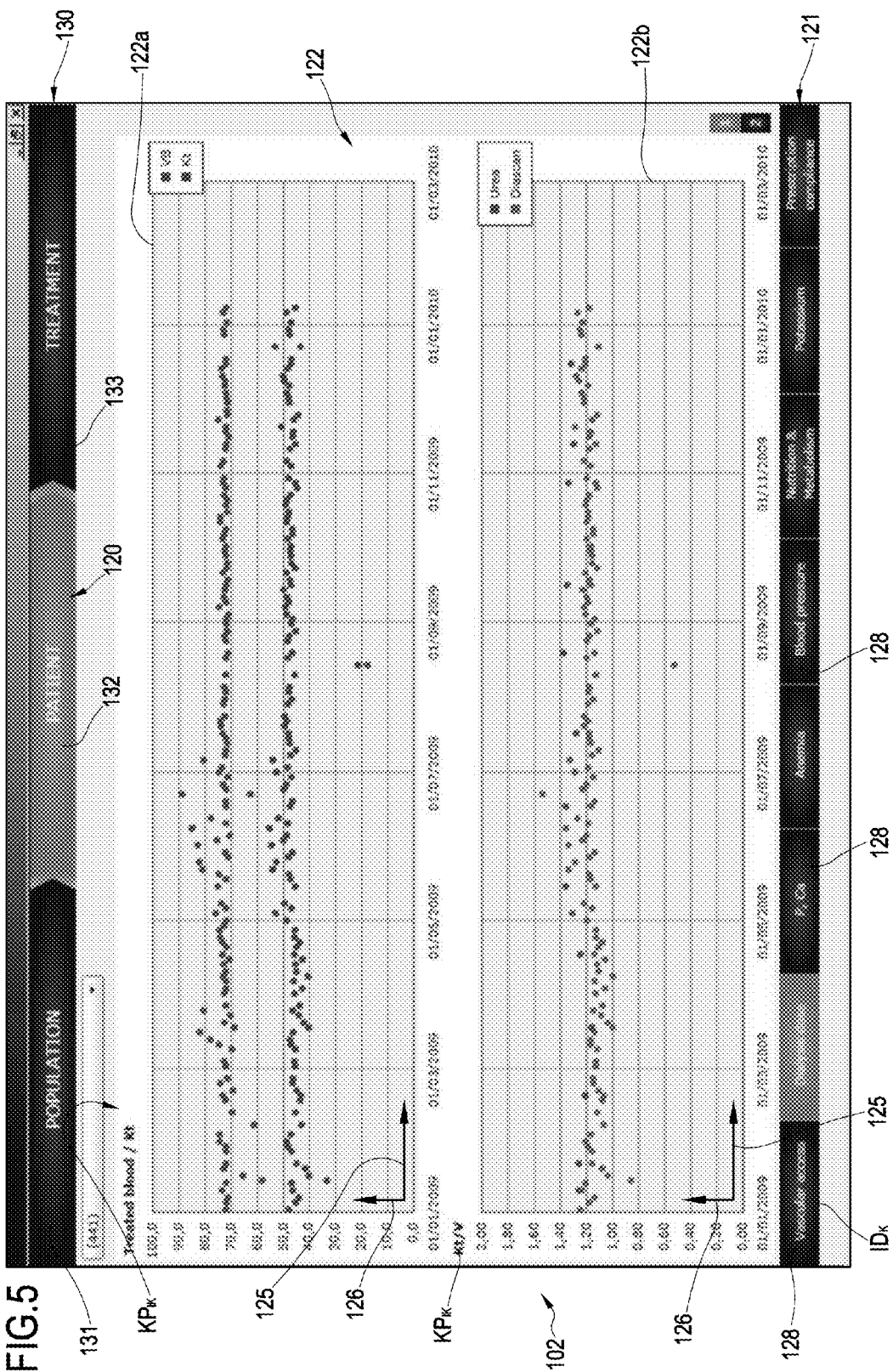
Figure 6:
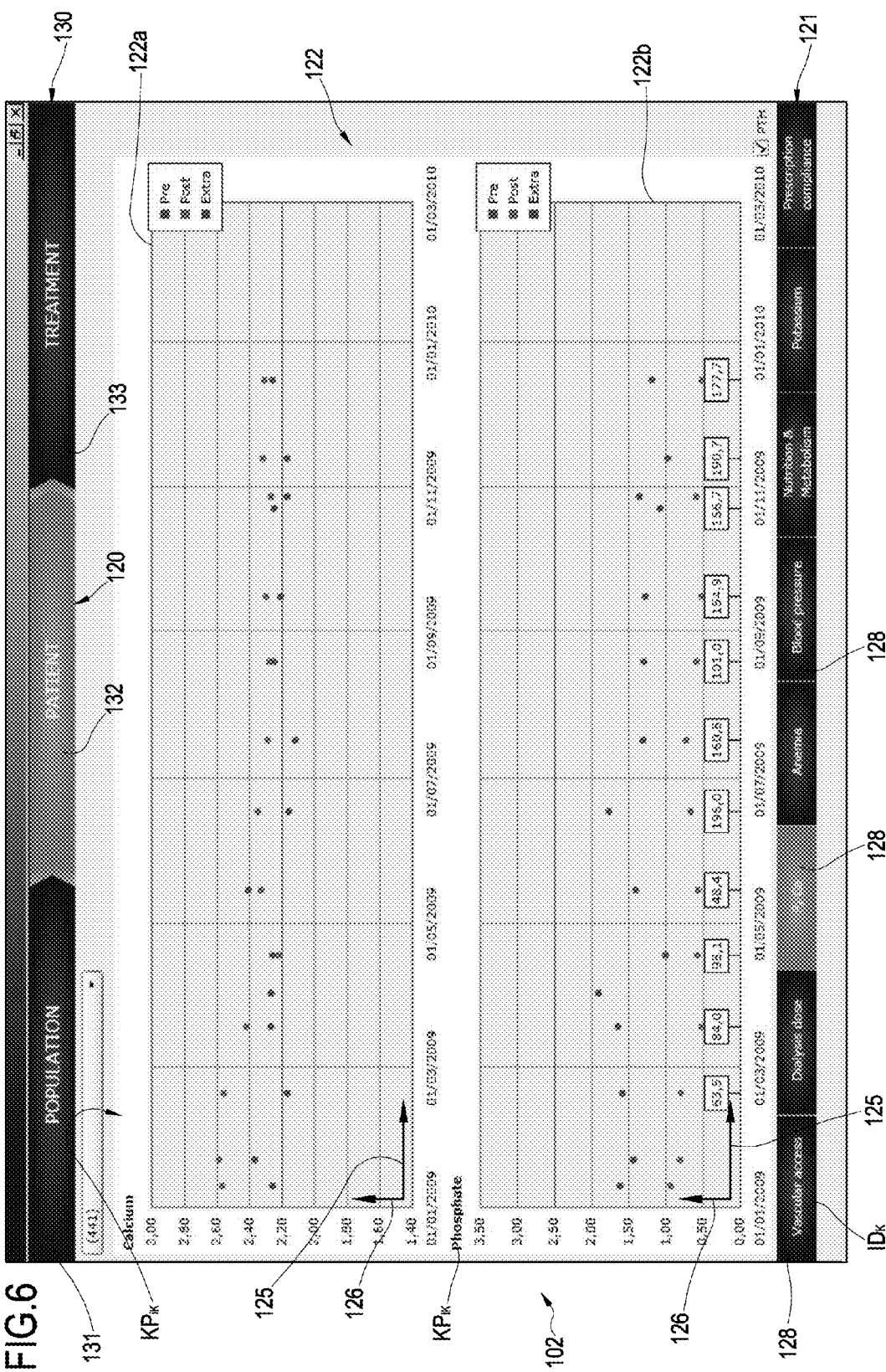
Figure 7:
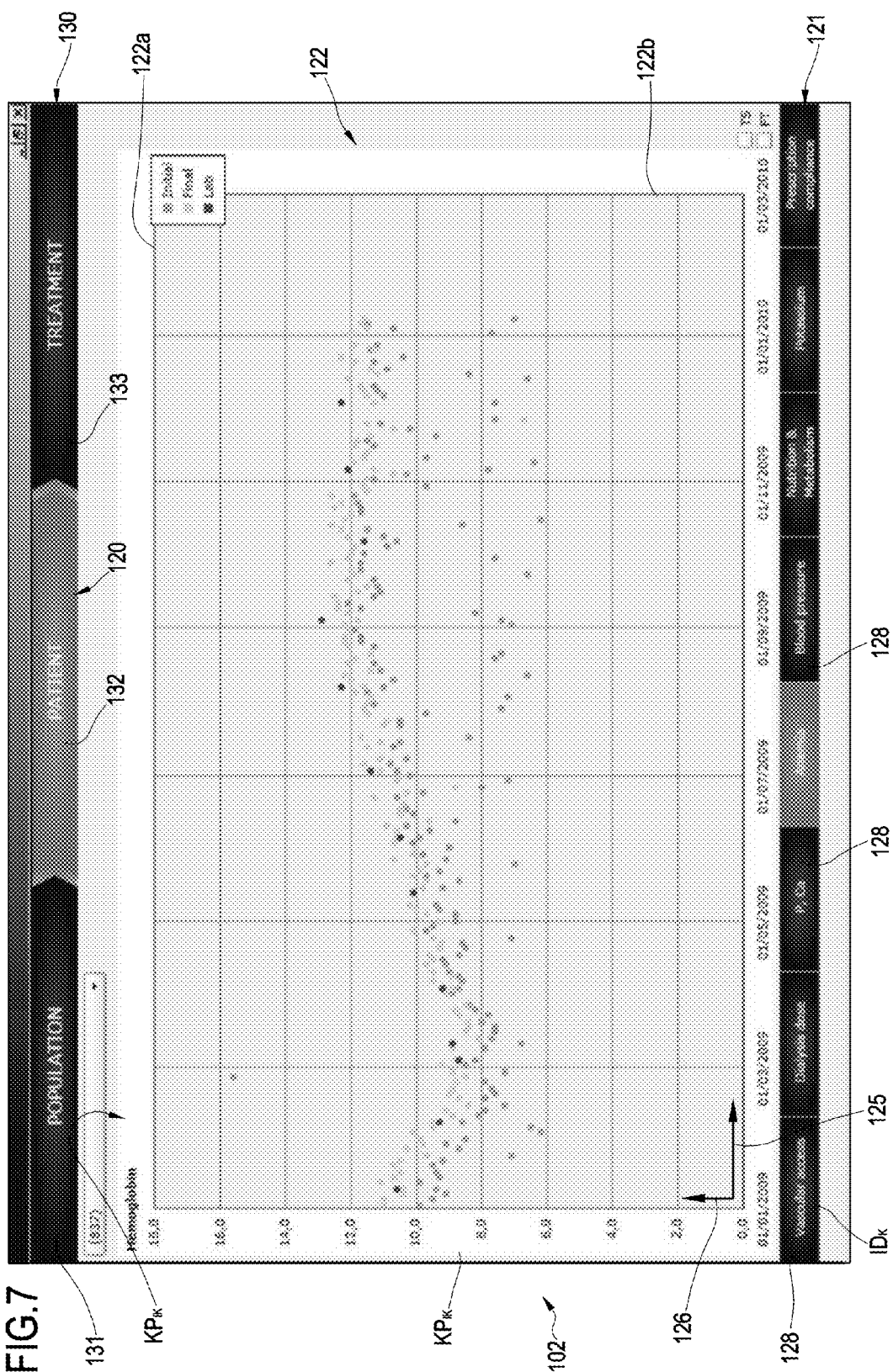
Figure 8:
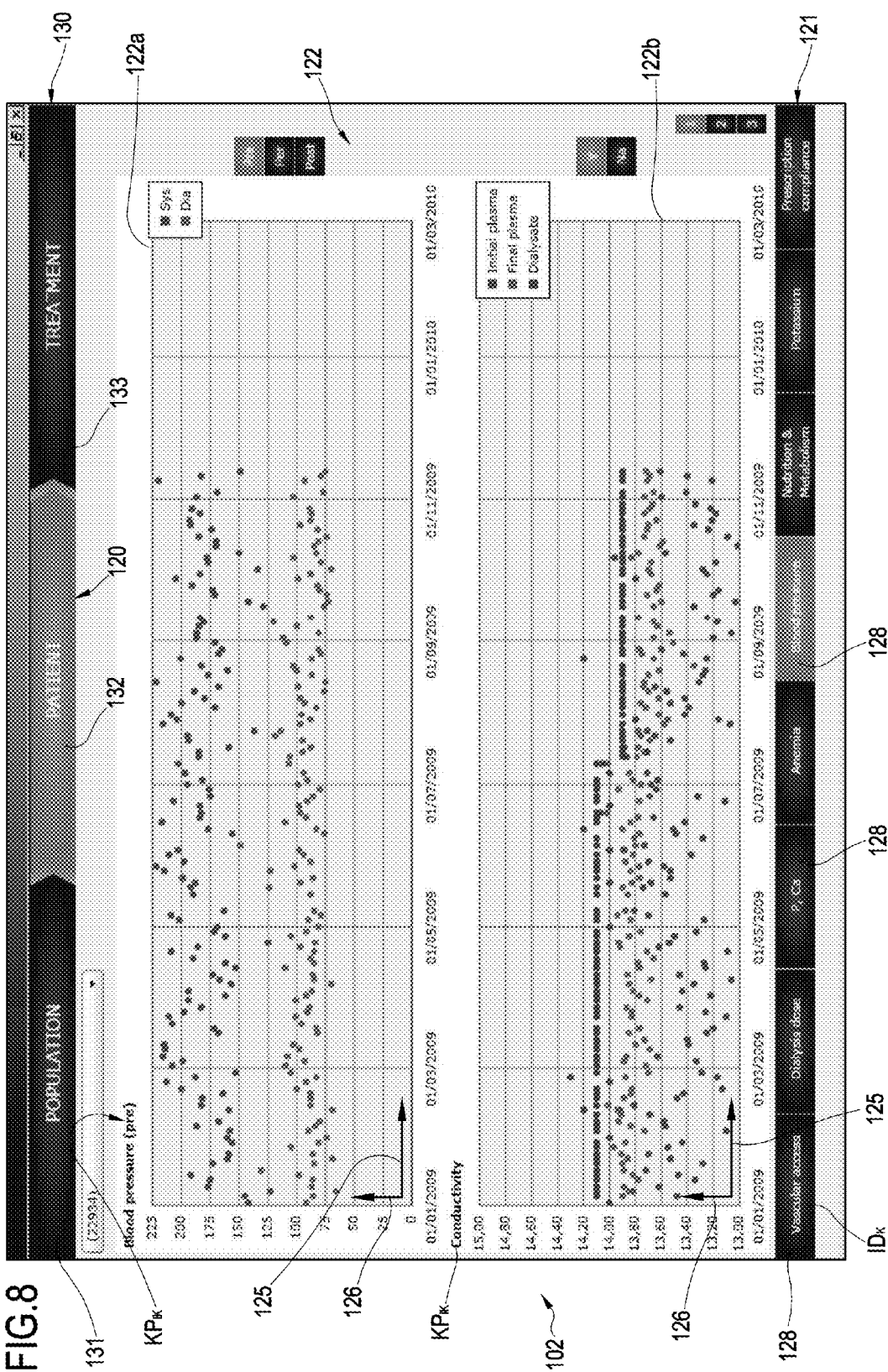

As it is shown in FIG. 4, the control unit may, in one or more embodiments, also be configured to calculate the sum and/or a mean value of the scores 164 for each monitored patient. Furthermore, the control unit may, in one or more embodiments, be configured to display the sum of scores 164 and/or to rank the patients from the one having highest score and thus highest risk of being problematic, to the one having lowest score, thus serving as a tool to drive operator (medical doctor or nurse) attention to those patients in the population of monitored patients really deserving immediate attention.

Going in further detail and again referring to FIG. 4, the control unit may, in one or more embodiments, be configured—when in said first display mode—to display a switching tool 170 for alternatively switching among and displaying one of the first display, the auxiliary display and the auxiliary display in recap format. In the embodiment shown, the switching tool 170 is represented by three selectable keys or buttons.

In one or more embodiments, the control unit 103 of each client 100 may be configured to allow setting of said time frame T to display, e.g. in said first display mode, a time frame selection tool 170 allowing to set at least one of: a start of said time frame (T), an end of said time frame (T), or both a start and an end of said time frame T.

The control unit 103 may, in one or more embodiments, also be configured to allow setting of a number of population filtration criteria and/or to store in said memory a plurality of pre-confectioned population filtration criteria. In both cases, the control unit may be configured to display in said first display mode a population filtration tool 180 for the setting of one population filtration criterion, detect the setting of a population filtration criterion and allow choosing one patient only among those satisfying the set population filtration criterion.

Note that in one or more embodiments, the population filtration criteria may be or include a condition concerning one or more of the values $KPV_i$ of selected the parameters $KP_i$. Alternatively, the population filtration criteria comprise conditions concerning one or more of said indicators $ID_k$. For instance, as acceptance criteria have been fixed for each indicator, a population filtration criterion may allow selecting patients within the monitored population which have a certain number of indicators not meeting the acceptability criteria. In accordance with a further alternative, the population filtration criteria may be based on the scores or on the mean value (as above described) of the scores: in other words, patients with a score satisfying a certain rule (e.g. a score mean value higher than a certain threshold) may be selected and data thereof allowed to be displayed.

Furthermore, in accordance with one or more embodiments, filtration criteria may concern the indicators: for instance an operator may be allowed to chose one or more indicators $ID_k$ of interest, and the client units receive and store in the apparatus memory 101, for each patient P, only the values $KPV_i$ contained in the hub module memory 201 taken, over the time frame T, by the subclass of said selected parameters $KP_{i,k}$ affecting the chosen indicators $ID_k$. This provision may help to focus on selected indicators only and to thereby transfer and elaborate only a reduced amount of data. The above criteria may also be combined: for instance the control unit may, in one or more embodiments, be configured to retain in the memory 101 and then use only data concerning a selected number of indicators and in particular only data concerning those patients having indicators falling out of the respective acceptability criteria, for the user to have the possibility to examine only potentially problematic patients and indicators.

Note that although in the present description the filtration criteria are executed by each control unit after transfer of the data from the hub module to client units, it may alternatively be envisaged that filtration criteria may, in one or more embodiments, be applied at the hub module before transferring data to each client unit 100.

Finally, in accordance with one or more embodiments, each client unit may also operate in a third display mode (see FIG. 11). Indeed, the control unit 103 may be configured to allow, when in said second display mode, a choice of one among the values taken by the parameters of said subclass of selected parameters $KP_{i,k}$ affecting the selected indicator $ID_k$. For instance referring to FIG. 3, the control unit 103 may allow selection of one of the values 123, for instance a value of the extracorporeal blood flow rate or of the dialysance; note that in the second display mode each value 123 relates to a single patient, namely the patient selected before switching from the first to the second mode. Selection of the value 123 may be done as above described in connection with selection of the graphic representations 113 in the first display mode and, for this reason, it is not repeated. Then the control unit establishes the treatment session corresponding to the chosen value 123 and to the chosen patient and, in one or more embodiments, activates the third display mode, comprising generating a third display 140 on said graphic user interface 102 having a third display field 142 showing, for the chosen patient and for the treatment session corresponding to the chosen value 123, a respective graphic representation 143 of plurality of values (for instance in table format) taken at different instants over session treatment time by a plurality parameters characteristic of a treatment session (e.g. time, extracorporeal blood flow rate $Q_B$, dialysance $D_Y$, plasmatic patient conductivity $C_P$, dialysate conductivity $C_D$, arterial and venous pressures $P_A$ and $P_V$, systolic and/or diastolic pressure, heart rate HR, blood volume, volume of treated blood and so on.

Connectivity

The control unit 103 may, in one or more embodiments, be configured to receive a copy of the information contained in the key parameter log or in memory 201 in various manners.

In one example, the control unit may remotely connect with the hub module and receive, at time intervals, the values $KPV_i$ of selected parameters $KP_i$ contained in a key parameter log 202 or in memory 201. For instance the control unit may, in one or more embodiments, be configured to interrogate the hub module at a plurality of regular time intervals during said time frame T in order to collect a plurality of sets of values $KPV_i$ of selected parameters $KP_i$, and thereby update the information displayed in the first and second display modes accordingly. In this case the control unit may include or be provided with a clock generator 103a for generating the interrogation times at which the control unit shall interrogate the hub module by generating an interrogation signal. Moreover, the control unit may be connected with a modem circuit 103b and with either an antenna 103c or with a wired connection for sending the interrogation signal to the hub module. Alternatively, the hub module may, in one or more embodiments, send a file or a number of files containing a copy of the content of the key parameter log 202 or a copy of the relevant data in memory 201 to each or to a number of client units via any available transmission channel: radiofrequency, World Wide Web, dedicated physical line and so on.

In a further alternative, the content of the key parameter log 202 or of memory 201 may, in one or more embodiments, be stored in a memory support, such a memory stick or a disk or a memory chip, which is then shipped to each client unit.

Furthermore, from a structural point of view it should be noted that, in one or more embodiments, hub module may be an independent hardware unit remotely located and communicatively connected with the blood treatment units and with the database units. In order to establish communication, the client units may, in one or more embodiments, include a modem device connected to the control unit and to an antenna for wireless connection or to a cable for wired connection with the hub module. On its turn, the hub module may, in one or more embodiments, be provided with a respective modem and with an antenna and or with a cable connection with units remote to the hub module.

In case one or two intermediate units are present, these intermediate units may, in one or more embodiments, also be independent hardware units remotely connected to the hub module and to the blood treatment units and/or laboratory database units. In such a case, also the intermediate units include a respective modem and an antenna or a cable connection for communicating with the other units of the systems 1, 1A.

In one alternative, however the hub module could, in one or more embodiments, be part of the intermediate unit 500 or of the further intermediate unit 501.

Process

One or more embodiments of a process of monitoring a plurality of patients over a time frame covering a plurality of blood treatment sessions are now described. The process may use the system comprising, in one or more embodiments, a plurality of client units, a hub module, laboratory databases and a plurality of blood treatment machines and optionally one or more intermediate units as above described. The process, in one or more embodiments, comprises collecting values V of a huge number of patient parameters (step 600 in FIGS. 13 and 14) and then execution of a number of steps at the hub module and at each client unit remotely located from the hub module. The collected values are then, in one or more embodiments, transmitted to the hub module (step 700), e.g. by the blood treatment machines and/or by one or more of the laboratory databases and/or by one or both the intermediate units 500 and 501.

Figure 13:
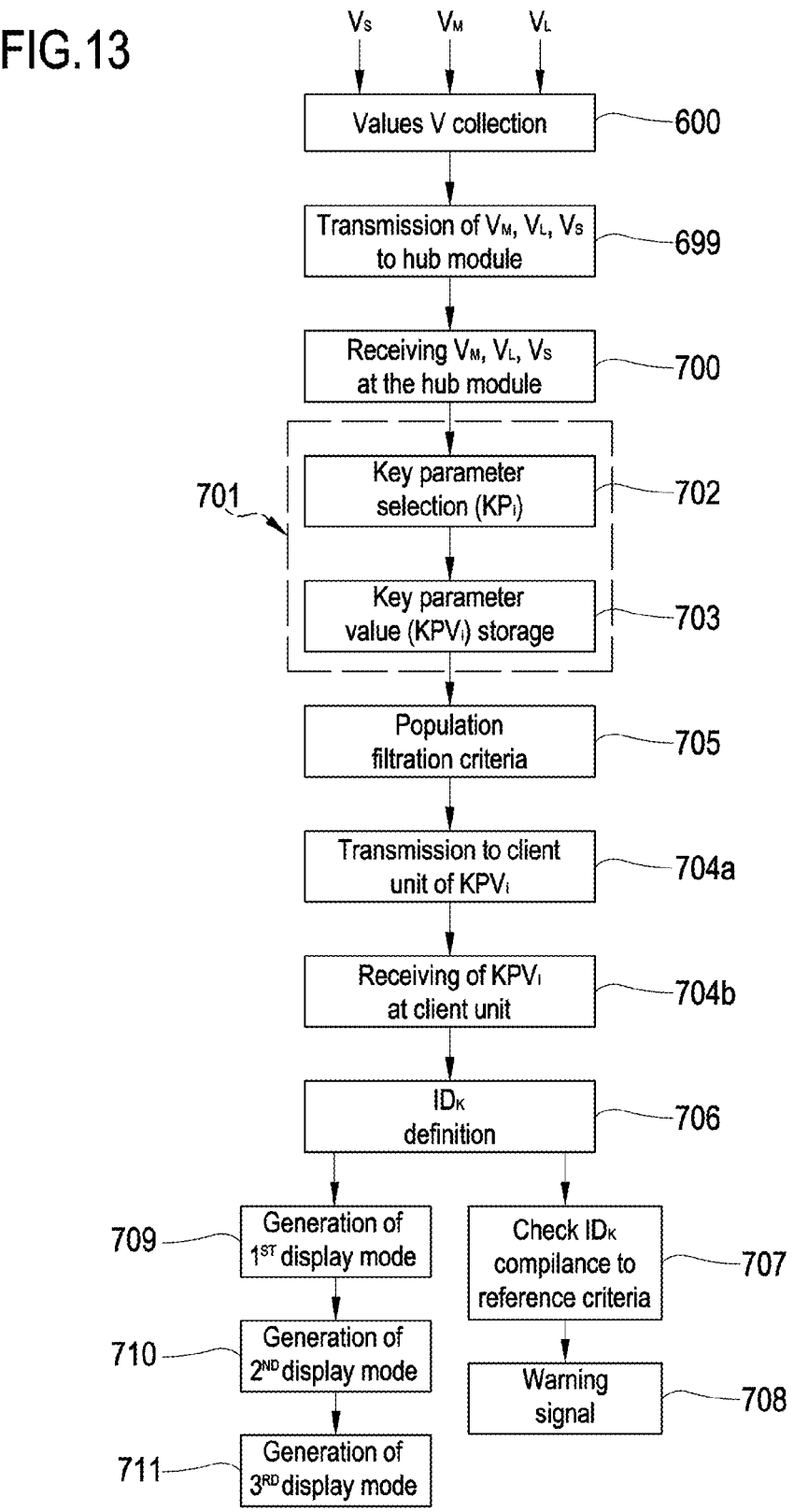
FIG. 13 shows a process of monitoring a plurality of patients undergoing extracorporeal blood treatment.

According to a first alternative shown in FIG. 13, the hub module 200 remotely connected to the blood treatment machines 300 and to laboratory storage units 400, executes, in one or more embodiments, the following process steps:

receiving (step 700) for each one of the plurality of patients, values V taken by a plurality of patient parameters at different time instants during the time frame T; the values of the plurality of patient parameters include, in one or more embodiments, for each patient:

values $V_M$ of a plurality of session parameters measured by sensors of blood treatment machines 300 during each blood treatment session of each patient over said time frame, values $V_L$ of a plurality of laboratory parameters obtained from tests conducted on fluid samples taken from each patient over said time frame T and stored in one or more laboratory storage units 400, set values $V_S$ of a plurality of prescription parameters set for each blood treatment session and each patient on each of said blood treatment machines 300 over said time frame, creating a key parameter log 202 (step 701) for storing the values $KPV_i$ of selected parameters $KP_i$, wherein creating, in one or more embodiments, comprises:

selecting (step 702) a first subgroup comprising, for each monitored patient, values of a selection of the plurality of session parameters $V_M$, selecting (step 702) a second subgroup comprising, for each monitored patient, set values of a selection of the plurality of prescription parameters $V_S$, selecting (step 702) a third subgroup comprising, for each monitored patient, values of a selection the plurality of laboratory parameters $V_L$, and storing (step 703) the selected key parameters values $KPV_i$.

The process then provides, in one or more embodiments, for a step of transmitting (step 704a) all or a subportion of the selected key parameters values $KPV_i$ and a step of receiving all or a subportion of the selected key parameters values $KPV_i$ at the client unit(s). As it is shown in FIG. 13, before transmitting the key parameter values, a step 705 of verifying one or more population filtration criteria may be carried out and then, in one or more embodiments, transmitting (step 704a) only those key parameter values concerning those patients satisfying the filtration criterion or criteria applied in step 705. In accordance with one or more embodiments, the population filtration criteria may be or include a condition concerning one or more of the values $KPV_i$ of selected the parameters $KP_i$. Alternatively, the population filtration criteria may, in one or more embodiments, comprise conditions concerning one or more of said indicators $ID_k$. For instance as acceptance criteria have been fixed for each indicator, then a population filtration criteria may be that of selecting patients among the population which have a certain number of indicators not meeting the acceptability criteria. In accordance with one or more further alternative embodiments, the population filtration criteria may be based on the scores or on the mean value of the scores. Note that instead of or in addition to population filtration criteria, the filtration criteria may, in one or more embodiments, relate to the indicators $ID_k$: for instance, for each patient P, only the values $KPV_i$ taken, over the time frame T, by the subclass of said selected parameters $KP_{i,k}$ affecting chosen indicators $ID_k$ may be transferred to the client units. This provision may help to focus on selected indicators only and to thereby transfer and elaborate only a reduced amount of data.

Alternatively, to what shown in FIG. 13, the filtration criterion or criteria may, in one or more embodiments, be applied after transfer of all key parameter values to the client units, i.e. after steps 704a and 704b takes place. In this case, the filtration criteria are executed by the client units.

As shown in FIG. 13, the following further process steps are, in one or more embodiments, executed at each of the client units:

defining, for each of said patients, a number of indicators $ID_k$ (step 706) wherein each of said indicator is distinct from the other and is defined based on the values $KPV_{i,k}$ taken by a respective sub-group $KP_{i,k}$ of said plurality of patient parameters $KP_i$ (the step of defining may, in one or more embodiments, alternatively be executed at the hub module);

assessing if the indicators (or a number of indicators) satisfy certain respective reference criteria (step 707); for example, this may be done by comparing values $KPV_{i,k}$ taken, over the time frame T, by the subclasses of selected parameters $KP_{i,k}$ affecting a same indicator $ID_k$ with the respective reference criteria (please refer to the section 'client units' for exemplifying reference criteria applicable to each of eight (8) indicators), signaling (708) whether or not one or more of said criteria are met.

At client units 100, the process may also or alternatively comprise, in one or more embodiments, execution of the following steps:

generating the first and second display modes (steps 709 and 710) and allowing switching between the two display modes.

At the client units, the process may also comprise, in one or more embodiments, generating a third display mode (step 711) which may be activated from the second display. The generation and switching among display modes, as well the features included in each display mode, correspond to what described in the above section 'client units' and thus are not further described in this section.

Figure 14:
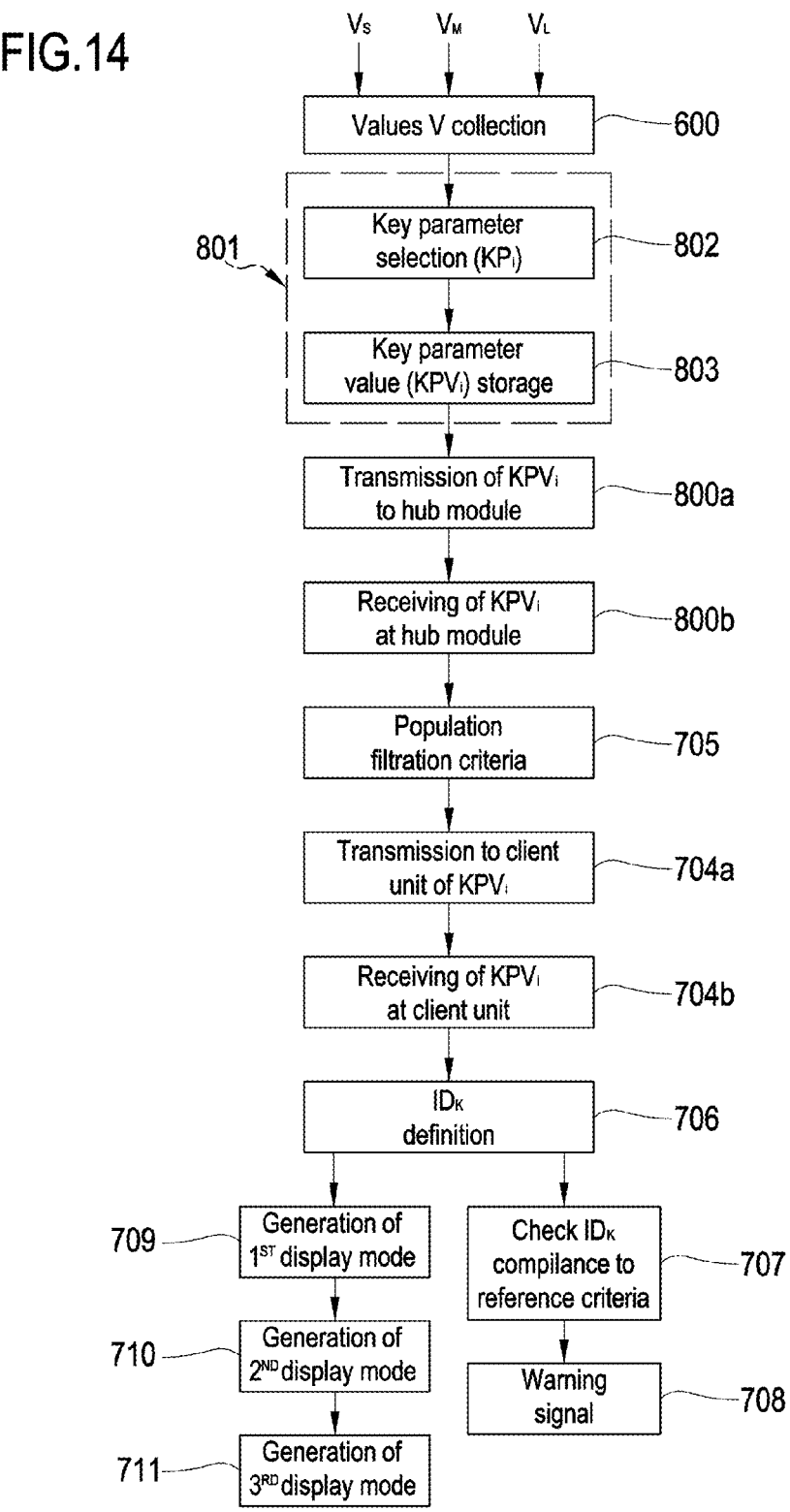
FIG. 14 shows another process of monitoring a plurality of patients undergoing extracorporeal blood treatment.

In the alternative process shown in FIG. 14, a step of collection of values V (step 600) as described for the process of FIG. 13 is provided in one or more embodiments. In detail, step 600 comprises collecting, for each one of the plurality of patients, values V taken by a plurality of patient parameters at different time instants during the time frame T; the values of the plurality of patient parameters include, in one or more embodiments, for each patient:

values $V_M$ of a plurality of session parameters measured by sensors of a blood treatment machine 300 during each blood treatment session of each patient over said time frame, values $V_L$ of a plurality of laboratory parameters obtained from tests conducted on fluid samples taken from each patient over said time frame T and stored in one or more laboratory storage units 400, set values $V_S$ of a plurality of prescription parameters set for each blood treatment session and each patient on each of said blood treatment machines 300 over said time frame.

Then, after step 600 and before actually transmitting (step 800a) collected data to the hub module, a scan is made, in one or more embodiments, of the collected values V for identifying values $KPV_i$ of selected parameters $KP_i$. In particular, the identification comprises:

selecting (step 802) a first subgroup comprising, for each monitored patient, values of a selection of the plurality of session parameters $V_M$, selecting (step 802) a second subgroup comprising, for each monitored patient, set values of a selection of the plurality of prescription parameters $V_S$, and selecting (step 802) a third subgroup comprising, for each monitored patient, values of a selection the plurality of laboratory parameters $V_L$.

The values $KPV_i$ of the selected parameters $KP_i$, may be stored, in one or more embodiments, either at one of the intermediate units or at the machines or at the laboratory databases or in part in one or more of the mentioned items (step 803). Then, differently from the process of FIG. 13, only the identified $KPV_i$ values are, in one or more embodiments, transferred (step 800a) to and then received at and stored by (step 804b) the hub module. Thus, according to the process of FIG. 14, in one or more embodiments, step 700 is not present and steps 701, 702, 703 are not executed at the hub module.

The further steps 705 to 711 of the process of FIG. 14 are analogous to those of the process of FIG. 13, have been identified by same reference numerals and not further described to avoid redundancy.

Control Units

In the above description, it has been indicated that, in one or more embodiments, a respective control or processing unit is located at the hub module, at each remote unit, at each blood treatment unit and at each laboratory database unit. From an architectural point of view, each of these units may, in one or more embodiments, comprise one or more programmable microprocessors or an analog type of control circuit or a combination thereof. In the case where the hub module is physically integrated into the intermediate unit 500 or into the further intermediate unit 501, then the control unit of the hub module and that of one of the units 501 or 500 may, in one or more embodiments, be a single control unit operating on at least two distinct software tasks in order to execute the activities of hub module and interfaces.

Although illustrative and exemplary embodiments of various apparatus, processes, and systems have been described herein, it is to be understood that the invention is not to be limited to the disclosed embodiments, but on the contrary, is intended to cover various modifications and equivalent arrangements included within the spirit and the scope of the appended claims.

Here below the components and corresponding reference numerals used in the detailed description are listed.

NUMBER PART

P Patients
1 System
100 Clients unit
101 Memory of client unit
102 Graphic user interface of client unit
103 Control unit of client unit
110 First display
111 First selection tool
112 First display field
113 Graphic representation
113a Point
113b Bar
113c Segment
114 Graphic selector
115 X-Axis in first display field
116 Y-Axis in first display field
120 Second display
121 Second selection tool
122 Second display field
122a Display area
122b Display area
122c Display area
123 Graphic representation
125 X-axis in second display field
126 Y-axis in second display field
128 Selectable zones
130 Menu area
131 First selectable area
132 Second selectable area
133 Third selectable area
142 Third display field
160 Auxiliary display
161 Table
162 List of monitored patients
163 List of indicators
164 Score
170 Switching tool
180 Population filtration tool
300 Blood treatment machines
301 Control unit of blood treatment machines
302 Sensors of blood treatment machines
303 Memory of blood treatment machines
305 Device connected to blood treatment machine
307 Actuator
310 Blood circuit
311 Blood chamber
312 Blood treatment unit
313 Dialysate chamber
315 Fresh dialysate preparation circuit
316 Spent dialysate liquid circuit
317 Waste discharge end
400 Lab storage unit
500 Intermediate elaborating unit
501 Further Intermediate elaborating unit

The invention claimed is:

1. A system for monitoring a plurality of patients affected by kidney failure over a time frame covering a plurality of blood treatment sessions, the system comprising:
a plurality of blood treatment machines for the treatment of the monitored patients, each blood treatment machine including at least one respective control unit and sensors for measuring session parameters, the control unit of each blood treatment machine being configured to:
receive from the sensors signals corresponding to values ($V_M$) of a plurality of session parameters measured during each blood treatment session for each patient, and
receive set values ($V_S$) of a plurality of prescription parameters, said set values of prescription parameters comprising values of a plurality of session parameters which are set on said blood treatment machines for the blood treatment sessions of each patient over said time frame (T);
a number of laboratory storage units configured to store values ($V_L$) of laboratory parameters relating to patient blood properties obtained from tests conducted on fluid samples taken from each patient;
a hub module communicatively connected to the blood treatment machines and to the laboratory storage units, the module comprising a control unit configured to:
receive from said blood treatment machines and for each monitored patient, values ($V_M$) of the plurality of session parameters measured by the sensors of each blood treatment machine during each blood treatment session of each patient over said time frame (T),
receive from said blood treatment machines and for each monitored patient, set values of ($V_S$) of prescription parameters set for each blood treatment session of each patient over said time frame,
receive from the laboratory storage units values ($V_L$) of laboratory parameters obtained from tests conducted on fluid samples taken from each patient over said time frame, and
create a key parameter log storing values ($KPV_i$) of selected parameters ($KP_i$) comprising:
values of a first subgroup of said plurality of session parameters ($V_M$),
set values of a second subgroup of the plurality of prescription parameters ($V_S$),
values of a third subgroup of said plurality of laboratory parameters ($V_L$); and
a plurality of client units each configured for reading the data coming from the key parameter log and each further configured to:
store, for each patient, the values ($KPV_i$) of the selected parameters ($KP_i$) contained in the key parameter log,
define, for each of said patients, a number of indicators ($ID_k$) wherein each of said indicator is distinct from the other and is defined based on the values ($KPV_{i,k}$) taken by a respective subclass ($KP_{i,k}$) of said selected parameters ($KP_i$),
compare the values ($KPV_{i,k}$) taken, over the time frame (T), by the subclasses of selected parameters ($KP_{i,k}$) affecting a same indicator ($ID_k$) with respective reference criteria;
signal whether one or more of said criteria are not met.

2. A system according to claim 1 wherein each client unit is further configured for interrogating at time intervals (t) the hub module and receiving either all or a prefixed number of the values ($KPV_i$) of the selected parameters ($KP_i$) contained in the hub module memory.

3. A system according to claim 1, wherein the hub module processing unit is further configured to transmit all or a prefixed number of the values ($KPV_i$) of the selected parameters ($KP_i$) to each of said client units.

4. A system according to claim 1, wherein the hub module processing unit is configured to receive from said blood treatment machines and for each monitored patient, set values of ($V_S$) of prescription parameters set for each blood treatment session of each patient over said time frame, said set values of prescription parameters comprising one or more of:
values of a plurality of session parameters set for blood treatment sessions of each patient over said time frame,
values representative of medicament prescriptions which have been imparted to each patient over said time frame,
values representative of one or more disposable items used during blood treatment sessions of each patient over said time frame.

5. A system according to claim 1, comprising an intermediate elaborating unit, the intermediate unit being communicatively interposed between the hub module and the blood treatment machines, wherein the values coming from a number of blood treatment apparatus are collected by the intermediate unit before being transmitted to the hub module, and wherein the intermediate unit is configured to transmit said collected values either at time intervals or upon request to the hub module.

6. A system according to claim 5, comprising a further intermediate elaborating unit, the further intermediate unit being communicatively interposed between the hub module and the number of laboratory storage units, wherein the values coming from a number of laboratory storage units are collected by the further intermediate unit before being transmitted to the hub module, and wherein the further intermediate unit is configured to transmit said collected values either at time intervals or upon request to the hub module, further wherein the hub module is one of:
physically remote from the intermediate unit,
physically remote from both the intermediate unit and the further intermediate unit,
physically part of the intermediate unit, this latter being remotely connected to the plurality of blood treatment machines,
physically part of the further intermediate unit, this latter being remotely connected to the plurality of laboratory storage units.

7. A system according to claim 1, wherein each client unit includes an apparatus of monitoring a plurality of patients (P) affected by kidney failure over a time frame (T), the apparatus comprising a memory, a graphic user interface, and a control unit connected to the memory and to graphic user interface, wherein the apparatus control unit is configured to:
operate in a first display mode comprising generating on said graphic user interface a first display having a first selection tool for choosing one among said selected parameters ($KP_i$) and a first display field showing, for each of a plurality of patients, a respective graphic representation of one or more significant values taken by the chosen parameter across said time frame (T);
operate in a second display mode comprising generating on said graphic user interface a second display having a second selection tool for choosing one among said indicators ($ID_k$) and a second display field showing, for one patient, a graphic representation of the values ($KPV_{i,k}$) taken, over the time frame (T), by the subclass of said selected parameters ($KP_{i,k}$) affecting the selected indicator ($ID_k$);
allow, when in said first display mode, choosing one patient and detecting selection of said one patient; and subsequently
activate said second display mode and display said second display on the graphic user interface wherein, in the second display mode, graphic representations are displayed of the values ($KPV_{i,k}$) taken, over the time frame (T), by the subclass of said selected parameters ($KP_{i,k}$) affecting the selected indicator ($ID_k$) and relating to the chosen patient.

8. A system according to claim 7, wherein the control unit is configured to hide said first display when said second display mode is activated.

9. A system according to claim 7 wherein the control unit is configured to display said the graphic representations in side by side relation in said first display field; wherein the control unit, in said first display mode, is configured to detect the patient chosen by detecting selection of one of said first graphic representations, and wherein detecting selection of one of said graphic representations comprises detecting overlapping of a graphic selector with the chosen one among said first graphic representations, the graphic selector graphically differentiating the chosen first graphic representation from the other first graphic representations displayed on the first display.

10. A system according to claim 7, wherein the control unit is configured to display a menu area comprising a plurality of selectable areas, the plurality of selectable areas comprising at least a first selectable area and a second selectable area, wherein the control unit is further configured to detect selection of the first selectable area and to activate the first display mode when the first selectable area is selected and wherein the control unit is further configured to detect selection of the second selectable area and to activate the second display mode when the second selectable area is selected, and wherein the control unit is configured to display the menu area both in said first and in said second display modes.

11. A system according to claim 10 wherein the first display field comprises a Cartesian representation where one axis represents the patients and one other axis represents the measure of the values taken by the selected parameters ($KP_i$), and wherein each of said first graphic representations comprises a representation of the mean value taken by the selected parameter across said time frame (T) and a graphic representation of a distribution of values taken by the selected parameter around said mean value.

12. A system according to claim 7 wherein the control unit, in said first display mode, is configured to display on said graphic user interface an auxiliary display comprising a table displaying a list of the monitored patients, the control unit being also configured to associate an identification code to each patient and to detect the patient chosen by detecting selection of the respective identification code.

13. A system according to claim 7 wherein the control unit, in said first display mode, is configured to display on said graphic user interface a recap display comprising a table displaying a list of monitored patients, a list of said indicators ($ID_k$), and a score associated to a number of indicators and patients, wherein each of the displayed scores is univocally associated to a respective patient and to a respective indicator ($ID_K$), the control unit being configured to calculate each one of said scores based on a comparison of each of the values ($KPV_{i,k}$) taken, for the respective patient, by the subclass of said selected parameters ($KP_{i,k}$) affecting the indicator ($ID_k$), with a respective reference criterion.

14. A system according to claim 7 wherein the second selection tool comprises a plurality of selectable zones, each of said selectable zones corresponding to a respective one of said indicators ($ID_k$), wherein the control unit is further configured to:
detect selection of one indicator by detecting selection of the corresponding selectable zone, and
display on said second display the graphic representations of the values ($KPV_{i,k}$) taken, over the time frame (T), by the subclass of said selected parameters ($KP_{i,k}$) affecting the selected indicator ($ID_k$) and relating to the chosen patient.

15. A system according to claim 7 wherein the control unit is configured to allow setting of said time frame (T), wherein the control unit is configured to display in said first display mode a time frame selection tool allowing the setting of at least one of:
a start of said time frame (T),
an end of said time frame (T),
a start and an end of said time frame (T), and
wherein said time frame (T) covers a plurality of blood treatment sessions.

16. A system according to claim 7 wherein the control unit is configured to allow setting of a population filtration criterion and wherein the control unit, when in said first display mode, is configured to display the respective graphic representation of said one or more significant values, only for those patients satisfying the set population filtration criterion.

17. A system according to claim 16, wherein the control unit, when in said first display mode, is configured to allow choosing one patient only among those satisfying the set population filtration criterion.

18. A system according to claim 17 wherein said population filtration criteria comprises one in the group of: a condition concerning one or more of the values ($KPV_i$) of selected the parameters ($KP_i$); conditions concerning one or more of said indicators ($ID_k$).

19. A system according to claim 7 wherein the control unit is configured to:
allow an operator to choose one or more indicators ($ID_k$) of interest,
receive and store in the apparatus memory, for each patient (P), only the values ($KPV_i$) contained in the hub module memory taken, over the time frame (T), by the subclass of said selected parameters ($KP_{i,k}$) affecting the chosen indicators ($ID_k$).

20. A system according to claim 7, wherein the control unit is configured to allow setting of a population filtration criterion and is configured to request a scan of the hub module memory, and receive and store in the apparatus memory exclusively the values ($KPV_i$) of selected parameters ($KP_i$) relating to patients satisfying the population filtration criterion.

21. A system according to claim 7 wherein the control unit is configured to:
allow, when in said second display mode, to chose one among the values taken by the parameters of said subclass of selected parameters ($KP_{i,k}$) affecting the selected indicator ($ID_k$);
establish the treatment session corresponding to the chosen value;
operate in a third display mode, comprising generating a third display on said graphic user interface having a third display field showing, for the chosen patient and for the treatment session corresponding to the chosen value, a respective graphic representation of a plurality of values taken at different instants over session treatment time by said a plurality parameters.

22. A system according to claim 7, wherein the control unit is configured to calculate a sum and/or a mean value of said scores referring to a same patient, and wherein the control unit is configured to rank patients from the one having highest score to the one having lowest score.

23. A system according to claim 1 wherein the values of the first subgroup of said plurality of session parameters ($V_M$) include measured values for one or more of the following parameters:
blood flow rate,
clearance or dialysance values,
treated blood volume,
K*Tr and or K*Tr/V where K is measured dialysance, Tr is treatment time and V a reference volume,
dialysate conductivity,
patient blood conductivity at the beginning and/or at the end of the treatment session,
transferred ionic mass,
total weight loss,
real session duration,
measures of cardiac parameters: systolic and diastolic arterial pressure (TA), cardiac rate,
arterial and/or venous pressure,
hemoglobin, e.g. obtained by calorimetric detection.

24. A system according to claim 1 wherein the set values of the second subgroup of said plurality of prescription parameters ($V_S$) include for each blood treatment session of each patient over said time frame T:
duration of the blood treatment session, blood conductivity,
blood flow rate,
patient's dry weight,
the calcium concentration for the dialysis liquid,
the potassium concentration for the dialysis liquid,
the blood flow rate in the extracorporeal circuit,
the weight loss rate,
the total weight loss to be achieved at the end of the treatment,
the blood conductivity to be achieved at the end of the treatment,
the dialysis dose.

25. A system according to claim 1 wherein the values of the third subgroup of the laboratory parameters ($V_L$) include values of:
Urea concentration (pre and/or post treatment session)
Creatinine concentration (pre and/or post treatment session)
Uric acid concentration (pre and/or post treatment session)
Sodium concentration (pre and/or post treatment session)
Potassium concentration (pre and/or post treatment session)
Bicarbonate concentration (pre and/or post treatment session)
Phosphate concentration (pre and/or post treatment session)
Calcium concentration (pre and/or post treatment session)
Total proteins concentration (pre and/or post treatment session)
PTH (parathyroid hormone)
Hemoglobin
Ferritin
Saturation coefficient
Albumin
CRP (C-reactive protein)
Total cholesterol
LDL cholesterol
Triglycerides
Glycemia
beta-2-microglobuline
Glycated hemoglobin
KT/V Urea
Systolic and diastolic arterial pressure (TA) measured while lying on a bed before and after treatment session
Weight before and after treatment session.

26. A system according to claim 1 wherein the indicators comprise from four (4) to eight (8) of the following dialysis indicators:
a first indicator $ID_1$ relating to the conditions of the vascular access—this indicator uses a first subclass of the $KP_i$ including one or more of: measured values $KPV_M$ for the blood flow rate, for the ionic dialysance and for the arterial and venous pressures;
a second indicator $ID_2$ relating to the prescription conformity—this indicator uses a second subclass of the $KP_i$ including one or more of: prescription values $KPV_S$ for the duration of the treatment, the blood and/or dialysate conductivity, the blood flow rate, and the patient's dry weight, and measured values $KPV_M$ for the treated blood volume, for the dialysate conductivity, for the total weight loss and for the total session duration;
a third indicator $ID_3$ relating to potassium—this indicator uses a third subclass of the $KP_i$ including one or more of: prescription values $KPV_S$ for the dialysate potassium and laboratory parameter values $KPV_L$ for the potassium concentration in blood;
a fourth indicator $ID_4$ relating to anemia—this indicator uses a fourth subclass of the $KP_i$ including one or more of: measured values $KPV_M$ for hemoglobin and laboratory parameter values $KPV_L$ for hemoglobin, ferritin and saturation coefficient;
a fifth indicator $ID_5$ relating to nutrition and metabolism—this indicator uses a fifth subclass of the $KP_i$ including one or more of: laboratory parameter values $KPV_L$ bicarbonate, blood sugar, total proteins, albumin, CRP;
a sixth indicator $ID_6$ relating to phosphorous-calcium equilibrium—this indicator uses a sixth subclass of the $KP_i$ including one or more of: laboratory parameter values $KPV_L$ for phosphate, calcium, PTH;
a seventh indicator $ID_7$ relating to hypertension—this indicator uses a seventh subclass of the $KP_i$ including one or more of: prescription values $KPV_S$ for plasmatic conductivity (initial and/or final) and for dialysate conductivity; laboratory parameter values $KPV_L$ for sodium concentration in blood (before and/or after treatment), cardiac parameters (systolic and diastolic pressure, heart rate), weight before and after treatment; and measured values $V_M$ for dialysate conductivity, blood conductivity before and after treatment session, ionic mass transfer, total weight loss, cardiac parameter measures (systolic and diastolic pressure and heart rate);
an eighth indicator $ID_8$ relating to dialysis dose—this indicator uses an eight subclass of the $KP_i$ including one or more of: laboratory parameter values $KPV_L$ for urea and creatinine concentration in blood pre and post session and for beta-2-microglobuline and KT/V urea; and measured values $V_M$ for the total treated blood volume and the measured KT and KT/K;
wherein the control unit of each of the client units compares each of the values ($KPV_{i,k}$) taken, over the time frame T, by the subclasses of selected parameters ($KP_{i,k}$) affecting a same indicator IDk with respective reference criteria and detects possible drifts compared to what is regarded as a reference criterion of normality.

27. A system according to claim 26 wherein the control unit is configured to apply one or more of the following reference criteria in order to classify if the patient's status for each single IDk is acceptable, not acceptable or lies in an area uncertainty:
for the first indicator $ID_1$: the ionic dialysance measured values are compared with a reference; the patient's status is considered acceptable if the last 3 measures are > than 165 ml/min, not acceptable if the last 3 measures are < than 155 ml/min, and potentially critical in all other cases;
for the second indicator $ID_2$: the status is considered acceptable if the measured values for the parameters affecting this indicator are identical or fall within a strict acceptable range compared to the respective set values;
for the third indicator $ID_3$: the patient's status is considered acceptable if the last 3 measures for the potassium concentration in blood are < than 5.5 mmol/l, not acceptable if the last 3 measures for the potassium concentration in blood are > than 5.5 mmol/l, and potentially critical in all other cases;
for the fourth indicator $ID_4$: the patient's status is considered acceptable if the last 3 values for hemoglobin fall within 10 and 12 g/l; the patient's status is considered not acceptable if the last 3 values for hemoglobin are either above 13 g/l or below 10 g/l; the patient's status is considered potentially critical in all other cases;

for the fifth indicator $ID_5$: the patient's status is considered acceptable if the following conditions are all met:
albumin concentration >32 g/l,
urea concentration >1.1 g/l,
creatinine concentration >60 mg/l,
phosphorus concentration >34 mg/l,
potassium concentration >4.5 mmol/l;
the patient's status is considered not acceptable if the following conditions are all not met:
albumin concentration <32 g/l,
urea concentration <1.1 g/l,
creatinine concentration <60 mg/l,
phosphorus concentration <34 mg/l,
potassium concentration <4.5 mmol/l;
the patient's status is considered potentially critical in all other cases;

for the sixth indicator $ID_6$: the laboratory values for phosphorous, calcium and PTH are compared with respective references; the patient's status is considered acceptable if the last 3 values for phosphorous lie within 34 and 60 mg/l, and the last 3 values for calcium lie within 88 and 100 mg/l, and PTH last value is comprised within 100 and 300 μg/l; the patient's status is considered not acceptable if the last 3 values for phosphorous are above 60 mg/l; the situation is considered potentially critical in all other cases;

for the seventh indicator $ID_7$: the patient's status is considered not acceptable if the last 3 values for pre-dialysis session arterial pressure TA are above 170 mm Hg; the patient's status is considered acceptable if the last 3 values for pre-dialysis session arterial pressure TA are below 150 mm Hg; the patient's status is considered potentially critical in all other cases;

for the eight indicator $ID_8$: the measured KT values are compared with a reference; the patient status is considered acceptable if the last 3 measures are > than 40 liters, not acceptable if the last 3 measures are < than 36 ml/min, and potentially critical in all other cases. In case of less than 3 measures in the last 15 days, then the assessment is not considered reliable and discarded.

28. A system according to claim 1 wherein said set values ($V_S$) of a plurality of prescription parameters include one or more of:
values of a plurality of session parameters set for blood treatment sessions of each patient over said time frame,
values representative of medicament prescriptions which have been imparted to each patient over said time frame, and
values representative of one or more disposable items used during blood treatment sessions of each patient over said time frame.

29. A system according to claim 1, wherein, to signal whether one or more of said criteria are not met, the plurality of client units are each further configured to activate an alarm in response to one or more of said criteria not being met.

30. A system according to claim 1, wherein each client unit includes an apparatus of monitoring a plurality of patients (P) affected by kidney failure over a time frame (T), the apparatus comprising a memory, a graphic user interface, and a control unit connected to the memory and to graphic user interface, wherein, to signal whether one or more of said criteria are not met, the apparatus control unit of the plurality of client units are each further configured to indicate via the graphic user interface whether each criterion of the one or more said criteria is non-acceptable or only potentially susceptible of being problematic.

\* \* \* \* \*